(12) United States Patent
Carfi et al.

(10) Patent No.: US 10,167,321 B2
(45) Date of Patent: Jan. 1, 2019

(54) CYTOMEGALOVIRUS ANTIGENS AND USES THEREOF

(71) Applicant: GLAXOSMITHKLINE BIOLOGICALS, SA, Rixensart (BE)

(72) Inventors: Andrea Carfi, Cambridge, MA (US); Claudio Ciferri, Oakland, CA (US); Yi Xing, Andover, MA (US)

(73) Assignee: GLAXOSMITHKLINE BIOLOGICALS, SA (BE)

( * ) Notice: Subject to any disclaimer, the term of this patent is extended or adjusted under 35 U.S.C. 154(b) by 0 days.

(21) Appl. No.: 15/544,730

(22) PCT Filed: Jan. 22, 2016

(86) PCT No.: PCT/IB2016/050335
§ 371 (c)(1),
(2) Date: Jul. 19, 2017

(87) PCT Pub. No.: WO2016/116904
PCT Pub. Date: Jul. 28, 2016

(65) Prior Publication Data
US 2017/0369532 A1 Dec. 28, 2017

(30) Foreign Application Priority Data
Jan. 22, 2015 (EP) .................................... 15152221

(51) Int. Cl.
| C12N 7/00 | (2006.01) |
| A61K 38/00 | (2006.01) |
| A61K 39/00 | (2006.01) |
| A61K 39/12 | (2006.01) |
| A61K 39/25 | (2006.01) |
| A61K 39/42 | (2006.01) |
| C07K 16/08 | (2006.01) |
| C12N 15/86 | (2006.01) |
| A61K 39/245 | (2006.01) |
| C07K 14/005 | (2006.01) |

(52) U.S. Cl.
CPC ............ *C07K 14/005* (2013.01); *A61K 39/12* (2013.01); *A61K 39/245* (2013.01); *C07K 16/082* (2013.01); *A61K 38/00* (2013.01); *A61K 39/00* (2013.01); *A61K 39/25* (2013.01); *A61K 39/42* (2013.01); *A61K 2039/525* (2013.01); *A61K 2039/55566* (2013.01); *C07K 16/081* (2013.01); *C12N 7/00* (2013.01); *C12N 2710/16122* (2013.01); *C12N 2710/16134* (2013.01); *C12N 2710/16151* (2013.01)

(58) Field of Classification Search
CPC ...... A61K 39/12; A61K 39/245; A61K 38/00; A61K 39/00; A61K 2039/525; A61K 39/25; A61K 39/42; C12N 2710/16134; C12N 2710/16151; C12N 2710/16122; C12N 7/00; C12N 15/86; C12N 2710/16143; C12N 2710/16121; C12N 2710/16161; C12N 2810/6009; C07K 14/005; C07K 16/088; C07K 16/081; C07K 2319/50

See application file for complete search history.

(56) References Cited

U.S. PATENT DOCUMENTS 7,704,510 B2    4/2010   Shenk et al.

FOREIGN PATENT DOCUMENTS

| WO | WO 2012051211 | 4/2012 | |
| WO | WO 2014005959 | 1/2014 | |
| WO | WO-2014005959 A1 * | 1/2014 | ........... A61K 39/245 |
| WO | WO 2016067239 | 5/2016 | |
| WO | WO 2016116905 | 7/2016 | |

OTHER PUBLICATIONS

Davison AJ and McGregor A. Envelope glycoprotein L [Human herpesvirus 5]. GenBank: ADE88099.1, Dep. Apr. 10, 2010.*
PeptideCutter by ExPASy. https://web.expasy.org/cgi-bin/peptide_cutter/peptidecutter.pl, accessed Apr. 12, 2018.*
European Patent Office as International Searching Authority, International Search Report and Written Opinion for International Application No. PCT/IB2016/050335, 10 pages, dated May 10, 2016.
Wen et al., *Human cytomegalovirus gH/gL/UL128/UL130/UL131A complex elicits potently neutralizing antibodies in mice*, 2014 Vaccine 32(30): 3796-3804.
Ryckman et al., *Characterization of the human cytomegalovirus gH/gL/Ul128-131 complex that mediates entry into epithelial and endothelial cells*, 2008 J. Virol. 82(1):60-70.
Ciferri et al., *Structural and biochemical studies of HCMV gH/gL/gO and pentamer reveal mutually exclusive cell entry complexes*, 2015 PNAS 112(6): 1767-1772.
Adler, *Immunization to prevent congenital cytomegalovirus infection*, 2013 Br. Med. Bull. 107(1): 57-68.
Saccoccio et al., *Peptides from cytomegalovirus UL130 and Ul131 proteins induce high titer antibodies that block viral entry into mucosal epithelial cells*, 2011 Vaccine 29: 2705-2711.
Pass et al., *Vaccine prevention of material cytomegalovirus infection*, 2009 N. Engl. J. Med. 360: 1191-1199.
Wussow et al., *A Vaccine Based on the Rhesus Cytomegalovirus UL128 Complex Induces Broadly Neutralizing Antibodies in Rhesus Macaques*, 2013 J. Virol. 87(3): 1322-1332.
Davison et al., *The Human Cytomegalovirus Genome Revisited: Comparison with the Chimpanzee Cytomegalovirus Genome*, 2003 J. Gen. Virol. 84: 17-28.

* cited by examiner

Primary Examiner — Rachel B Gill

(57) ABSTRACT

This disclosure provides modified cytomegalovirus (CMV) gL proteins and complexes comprising gL proteins. The modified gL proteins remain intact and are able to form complexes with other CMV proteins.

60 Claims, 4 Drawing Sheets

Specification includes a Sequence Listing.

SEQUENCE LISTING

<160> NUMBER OF SEQ ID NOS: 27

<210> SEQ ID NO 1
<211> LENGTH: 278
<212> TYPE: PRT
<213> ORGANISM: Human herpesvirus 5

<400> SEQUENCE: 1

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys

```
                    50                  55                  60
Tyr Glu Ser Trp Leu Arg Pro Leu Val Asn Val Thr Gly Arg Asp Gly
 65                  70                  75                  80

Pro Leu Ser Gln Leu Ile Arg Tyr Arg Pro Val Thr Pro Glu Ala Ala
                 85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Gly Tyr Ser Glu Cys
        130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Pro Glu Gly Ile Thr Leu Phe Tyr Gly
210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 2
<211> LENGTH: 278
<212> TYPE: PRT
<213> ORGANISM: Human herpesvirus 5

<400> SEQUENCE: 2

Met Cys Arg Arg Pro Asp Cys Gly Phe Ser Phe Ser Pro Gly Pro Val
  1               5                  10                  15

Ala Leu Leu Trp Cys Cys Leu Leu Leu Pro Ile Val Ser Ser Ala Thr
                 20                  25                  30

Val Ser Val Ala Pro Thr Val Ala Glu Lys Val Pro Ala Glu Cys Pro
             35                  40                  45

Glu Leu Thr Arg Arg Cys Leu Leu Gly Glu Val Phe Gln Gly Asp Lys
         50                  55                  60

Tyr Glu Ser Trp Leu Arg Pro Leu Val Asn Val Thr Arg Arg Asp Gly
 65                  70                  75                  80

Pro Leu Ser Gln Leu Ile Arg Tyr Arg Pro Val Thr Pro Glu Ala Ala
                 85                  90                  95

Asn Ser Val Leu Leu Asp Asp Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Gly Tyr Ser Glu Cys
        130                 135                 140
```

```
Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
            165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
            195                 200                 205

Pro Val Ser Thr Ala Ala Pro Glu Gly Ile Thr Leu Phe Tyr Gly
        210                 215                 220

Leu Tyr Asn Ala Val Lys Glu Phe Cys Leu Arg His Gln Leu Asp Pro
225                 230                 235                 240

Pro Leu Arg His Leu Asp Lys Tyr Tyr Ala Gly Leu Pro Pro Glu
            245                 250                 255

Leu Lys Gln Thr Arg Val Asn Leu Pro Ala His Ser Arg Tyr Gly Pro
            260                 265                 270

Gln Ala Val Asp Ala Arg
        275
```

<210> SEQ ID NO 3
<211> LENGTH: 278
<212> TYPE: PRT
<213> ORGANISM: Human herpesvirus 5

<400> SEQUENCE: 3

```
Met Cys Arg Arg Pro Asp Cys Gly Phe Ser Phe Ser Pro Gly Pro Val
1               5                   10                  15

Val Leu Leu Trp Cys Cys Leu Leu Pro Ile Val Ser Ser Val Ala
            20                  25                  30

Val Ser Val Ala Pro Thr Ala Ala Glu Lys Val Pro Ala Glu Cys Pro
            35                  40                  45

Glu Leu Thr Arg Arg Cys Leu Leu Gly Glu Val Phe Gln Gly Asp Lys
    50                  55                  60

Tyr Glu Ser Trp Leu Arg Pro Leu Val Asn Val Thr Arg Arg Asp Gly
65                  70                  75                  80

Pro Leu Ser Gln Leu Ile Arg Tyr Arg Pro Val Thr Pro Glu Ala Ala
            85                  90                  95

Asn Ser Val Leu Leu Asp Asp Ala Phe Leu Asp Thr Leu Ala Leu Leu
            100                 105                 110

Tyr Asn Asn Pro Asp Gln Leu Arg Ala Leu Leu Thr Leu Leu Ser Ser
            115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
            165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
            195                 200                 205

Pro Val Ser Thr Ala Ala Pro Glu Gly Ile Thr Leu Phe Tyr Gly
        210                 215                 220

Leu Tyr Asn Ala Val Lys Glu Phe Cys Leu Arg His Gln Leu Asp Pro
225                 230                 235                 240
```

```
Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275

<210> SEQ ID NO 4
<211> LENGTH: 248
<212> TYPE: PRT
<213> ORGANISM: Human herpesvirus 5

<400> SEQUENCE: 4

Ala Ala Val Ser Val Ala Pro Thr Ala Ala Glu Lys Val Pro Ala Glu
1               5                   10                  15

Cys Pro Glu Leu Thr Arg Arg Cys Leu Leu Gly Glu Val Phe Glu Gly
            20                  25                  30

Asp Lys Tyr Glu Ser Trp Leu Arg Pro Leu Val Asn Val Thr Gly Arg
        35                  40                  45

Asp Gly Pro Leu Ser Gln Leu Ile Arg Tyr Arg Pro Val Thr Pro Glu
    50                  55                  60

Ala Ala Asn Ser Val Leu Leu Asp Glu Ala Phe Leu Asp Thr Leu Ala
65                  70                  75                  80

Leu Leu Tyr Asn Asn Pro Asp Gln Leu Arg Ala Leu Leu Thr Leu Leu
                85                  90                  95

Ser Ser Asp Thr Ala Pro Arg Trp Met Thr Val Met Arg Gly Tyr Ser
            100                 105                 110

Glu Cys Gly Asp Gly Ser Pro Ala Val Tyr Thr Cys Val Asp Asp Leu
        115                 120                 125

Cys Arg Gly Tyr Asp Leu Thr Arg Leu Ser Tyr Gly Arg Ser Ile Phe
    130                 135                 140

Thr Glu His Val Leu Gly Phe Glu Leu Val Pro Pro Ser Leu Phe Asn
145                 150                 155                 160

Val Val Val Ala Ile Arg Asn Glu Ala Thr Arg Thr Asn Arg Ala Val
                165                 170                 175

Arg Leu Pro Val Ser Thr Ala Ala Pro Glu Gly Ile Thr Leu Phe
            180                 185                 190

Tyr Gly Leu Tyr Asn Ala Val Lys Glu Phe Cys Leu Arg His Gln Leu
        195                 200                 205

Asp Pro Pro Leu Leu Arg His Leu Asp Lys Tyr Tyr Ala Gly Leu Pro
    210                 215                 220

Pro Glu Leu Lys Gln Thr Arg Val Asn Leu Pro Ala His Ser Arg Tyr
225                 230                 235                 240

Gly Pro Gln Ala Val Asp Ala Arg
                245

<210> SEQ ID NO 5
<211> LENGTH: 17
<212> TYPE: PRT
<213> ORGANISM: Human herpesvirus 5

<400> SEQUENCE: 5

Gly Arg Asp Gly Pro Leu Ser Gln Leu Ile Arg Tyr Arg Pro Val Thr
1               5                   10                  15

Pro
```

<210> SEQ ID NO 6
<211> LENGTH: 742
<212> TYPE: PRT
<213> ORGANISM: Human herpesvirus 5

<400> SEQUENCE: 6

```
Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
            20                  25                  30

Pro Leu Asp Lys Ala Phe His Leu Leu Asn Thr Tyr Gly Arg Pro
        35                  40                  45

Ile Arg Phe Leu Arg Glu Asn Thr Thr Gln Cys Thr Tyr Asn Ser Ser
50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
130                 135                 140

Gln Asp Ser Leu Gly Glu Gln Pro Thr Thr Val Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
370                 375                 380
```

```
Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
            405                 410                 415

Thr Ser Leu Val Arg Leu Val Tyr Ile Leu Ser Lys Gln Asn Gln Gln
        420                 425                 430

His Leu Ile Pro Gln Trp Ala Leu Arg Gln Ile Ala Asp Phe Ala Leu
    435                 440                 445

Lys Leu His Lys Thr His Leu Ala Ser Phe Leu Ser Ala Phe Ala Arg
450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
            485                 490                 495

Leu Ala Glu Leu Ser His Phe Thr Gln Leu Leu Ala His Pro His His
        500                 505                 510

Glu Tyr Leu Ser Asp Leu Tyr Thr Pro Cys Ser Ser Gly Arg Arg
    515                 520                 525

Asp His Ser Leu Glu Arg Leu Thr Arg Leu Phe Pro Asp Ala Thr Val
530                 535                 540

Pro Thr Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
            565                 570                 575

Ser Phe Ser Ala Leu Thr Val Ser Glu His Val Ser Tyr Val Val Thr
        580                 585                 590

Asn Gln Tyr Leu Ile Lys Gly Ile Ser Tyr Pro Val Ser Thr Thr Val
    595                 600                 605

Val Gly Gln Ser Leu Ile Ile Thr Gln Thr Asp Ser Gln Thr Lys Cys
610                 615                 620

Glu Leu Thr Arg Asn Met His Thr Thr His Ser Ile Thr Ala Ala Leu
625                 630                 635                 640

Asn Ile Ser Leu Glu Asn Cys Ala Phe Cys Gln Ser Ala Leu Leu Glu
            645                 650                 655

Tyr Asp Asp Thr Gln Gly Val Ile Asn Ile Met Tyr Met His Asp Ser
        660                 665                 670

Asp Asp Val Leu Phe Ala Leu Asp Pro Tyr Asn Glu Val Val Val Ser
    675                 680                 685

Ser Pro Arg Thr His Tyr Leu Met Leu Leu Lys Asn Gly Thr Val Leu
690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
            725                 730                 735

Arg Met Leu Lys Thr Cys
            740

<210> SEQ ID NO 7
<211> LENGTH: 6
<212> TYPE: PRT
<213> ORGANISM: Human herpesvirus 5

<400> SEQUENCE: 7

Asn Ser Val Leu Leu Asp
```

```
<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Asp Tyr Lys Asp Asp Asp Asp Lys
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ala Trp Arg His Pro Gln Phe Gly Gly
1               5

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Trp Ser His Pro Gln Phe Glu Lys
1               5

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 11

His His His His His His
1               5

<210> SEQ ID NO 12
<211> LENGTH: 40
<212> TYPE: PRT
<213> ORGANISM: Herpes simplex virus 2

<400> SEQUENCE: 12

Asp Asp Val Ser Trp Arg Tyr Glu Ala Pro Ser Val Ile Asp Tyr Ala
1               5                   10                  15

Arg Ile Asp Gly Ile Phe Leu Arg Tyr His Cys Pro Gly Leu Asp Thr
            20                  25                  30

Phe Leu Trp Asp Arg His Ala Gln
        35                  40
```

<210> SEQ ID NO 13
<211> LENGTH: 40
<212> TYPE: PRT
<213> ORGANISM: Herpes simplex virus 1

<400> SEQUENCE: 13

Asp Asp Leu Asp Trp Arg Tyr Glu Thr Pro Ser Ala Ile Asn Tyr Ala
1               5                   10                  15

Leu Ile Asp Gly Ile Phe Leu Arg Tyr His Cys Pro Gly Leu Asp Thr
            20                  25                  30

Val Leu Trp Asp Arg His Ala Gln
        35                  40

<210> SEQ ID NO 14
<211> LENGTH: 39
<212> TYPE: PRT
<213> ORGANISM: Varicella zoster virus

<400> SEQUENCE: 14

Glu Ala Trp Asp Tyr Ala Ala Pro Pro Val Ser Asn Leu Ser Glu Ala
1               5                   10                  15

Leu Ser Gly Ile Val Val Lys Thr Lys Cys Pro Val Pro Glu Val Ile
            20                  25                  30

Leu Trp Phe Lys Asp Lys Gln
        35

<210> SEQ ID NO 15
<211> LENGTH: 58
<212> TYPE: PRT
<213> ORGANISM: Human herpesvirus 5

<400> SEQUENCE: 15

Glu Gly Asp Lys Tyr Glu Ser Trp Leu Arg Pro Leu Val Asn Val Thr
1               5                   10                  15

Gly Arg Asp Gly Pro Leu Ser Gln Leu Ile Arg Tyr Arg Pro Val Thr
            20                  25                  30

Pro Glu Ala Ala Asn Ser Val Leu Leu Asp Glu Ala Phe Leu Asp Thr
        35                  40                  45

Leu Ala Leu Leu Tyr Asn Asn Pro Asp Gln
    50                  55

<210> SEQ ID NO 16
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Gly Asp Lys Tyr Glu Ser Trp Leu Arg Pro Leu Val Asn Val Thr
1               5                   10                  15

Glu Ala Leu Ser Gly Val Leu Leu Asp Glu Ala Phe Leu Asp Thr Leu
            20                  25                  30

Ala Leu Leu Tyr Asn Asn Pro Asp Gln
        35                  40

<210> SEQ ID NO 17
<211> LENGTH: 48
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Gly Asp Lys Tyr Glu Ser Trp Leu Arg Pro Leu Val Asn Val Thr
1               5                   10                  15

Gly Arg Asp Gly Pro Leu Ser Glu Ala Leu Ser Gly Val Leu Leu Asp
            20                  25                  30

Glu Ala Phe Leu Asp Thr Leu Ala Leu Leu Tyr Asn Asn Pro Asp Gln
        35                  40                  45

<210> SEQ ID NO 18
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Gly Asp Lys Tyr Glu Ser Trp Leu Arg Pro Leu Val Asn Val Thr
1               5                   10                  15

Gly Arg Asp Gly Pro Leu Ser Gln Leu Ile Arg Tyr Arg Pro Val Thr
            20                  25                  30

Pro Glu Ala Leu Ser Gly Val Leu Leu Asp Glu Ala Phe Leu Asp Thr
        35                  40                  45

Leu Ala Leu Leu Tyr Asn Asn Pro Asp Gln
    50                  55

<210> SEQ ID NO 19
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Gly Asp Lys Tyr Glu Ser Trp Leu Arg Pro Leu Val Asn Val Thr
1               5                   10                  15

Gly Arg Asp Gly Pro Leu Ser Gln Leu Ile Arg Tyr Arg Pro Val Thr
            20                  25                  30

Pro Glu Ala Ala Ser Val Leu Leu Asp Glu Ala Phe Leu Asp Thr Leu
        35                  40                  45

Ala Leu Leu Tyr Asn Asn Pro Asp Gln
    50                  55

<210> SEQ ID NO 20
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Glu Gly Asp Lys Tyr Glu Ser Trp Leu Arg Pro Leu Val Asn Val Thr
1               5                   10                  15

-continued

Gly Arg Asp Gly Pro Leu Ser Gln Leu Ile Arg Tyr Arg Pro Val Thr
            20                  25                  30

Pro Glu Ala Ser Ser Thr Val Leu Leu Asp Glu Ala Phe Leu Asp Thr
        35                  40                  45

Leu Ala Leu Leu Tyr Asn Asn Pro Asp Gln
    50                  55

<210> SEQ ID NO 21
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Gly Asp Lys Tyr Glu Ser Trp Leu Arg Pro Leu Val Asn Val Thr
1               5                   10                  15

Gly Arg Asp Gly Pro Leu Ser Gln Leu Ile Arg Tyr Arg Pro Val Thr
            20                  25                  30

Pro Glu Ala Leu Ser Gly Ile Leu Leu Asp Glu Ala Phe Leu Asp Thr
        35                  40                  45

Leu Ala Leu Leu Tyr Asn Asn Pro Asp Gln
    50                  55

<210> SEQ ID NO 22
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Glu Gly Asp Lys Tyr Glu Ser Trp Leu Arg Pro Leu Val Asn Val Thr
1               5                   10                  15

Gly Arg Asp Gly Pro Leu Ser Gln Leu Ile Arg Tyr Arg Pro Val Thr
            20                  25                  30

Pro Glu Ala Ile Glu Val Val Leu Leu Asp Glu Ala Phe Leu Asp Thr
        35                  40                  45

Leu Ala Leu Leu Tyr Asn Asn Pro Asp Gln
    50                  55

<210> SEQ ID NO 23
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Glu Gly Asp Lys Tyr Glu Ser Trp Leu Arg Pro Leu Val Asn Val Thr
1               5                   10                  15

Gly Arg Asp Gly Pro Leu Ser Gln Leu Ile Arg Tyr Arg Pro Val Thr
            20                  25                  30

Pro Glu Ala Ile Asp Gly Val Leu Leu Asp Glu Ala Phe Leu Asp Thr
        35                  40                  45

Leu Ala Leu Leu Tyr Asn Asn Pro Asp Gln
    50                  55

<210> SEQ ID NO 24
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Glu Gly Asp Lys Tyr Glu Ser Trp Leu Arg Pro Leu Val Asn Val Thr
1               5                   10                  15

Gly Arg Asp Gly Pro Leu Ser Gln Leu Ile Arg Tyr Arg Pro Val Thr
            20                  25                  30

Pro Glu Ala Leu Ala Ile Val Leu Leu Asp Glu Ala Phe Leu Asp Thr
        35                  40                  45

Leu Ala Leu Leu Tyr Asn Asn Pro Asp Gln
    50                  55

<210> SEQ ID NO 25
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Gly Asp Lys Tyr Glu Ser Trp Leu Arg Pro Leu Val Asn Val Thr
1               5                   10                  15

Gly Arg Asp Gly Pro Leu Ser Gln Leu Ile Arg Tyr Arg Pro Val Thr
            20                  25                  30

Pro Glu Asn Leu Tyr Phe Gln Gly Val Leu Leu Asp Glu Ala Phe Leu
        35                  40                  45

Asp Thr Leu Ala Leu Leu Tyr Asn Asn Pro Asp Gln
    50                  55                  60

<210> SEQ ID NO 26
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Gly Asp Lys Tyr Glu Ser Trp Leu Arg Pro Leu Val Asn Val Thr
1               5                   10                  15

Gly Arg Asp Gly Pro Leu Ser Gln Leu Ile Arg Tyr Arg Pro Val Thr
            20                  25                  30

Pro Glu Ala Leu Ser Gly Ile Val Val Asp Glu Ala Phe Leu Asp Thr
        35                  40                  45

Leu Ala Leu Leu Tyr Asn Asn Pro Asp Gln
    50                  55

<210> SEQ ID NO 27
<211> LENGTH: 4
<212> TYPE: PRT

```
<213> ORGANISM: Human herpesvirus 5

<400> SEQUENCE: 27

Val Thr Pro Glu
1
```

CYTOMEGALOVIRUS ANTIGENS AND USES THEREOF

SEQUENCE LISTING

The instant application contains a Sequence Listing which has been submitted electronically in ASCII format and is hereby incorporated by reference in its entirety. Said ASCII copy, created on Jan. 14, 2016, is named VN056504WO_SL.txt and is 26,466 bytes in size.

FIELD OF THE INVENTION

This invention is in the field of cytomegalovirus (CMV) antigens that can be used for vaccines.

BACKGROUND OF THE INVENTION

Cytomegalovirus is a genus of virus that belongs to the viral family known as Herpesviridae or herpesviruses. The species that infects humans is commonly known as human cytomegalovirus (HCMV) or human herpesvirus-5 (HHV-5). Within Herpesviridae, HCMV belongs to the Betaherpesvirinae subfamily, which also includes cytomegaloviruses from other mammals.

Although they may be found throughout the body, HCMV infections are frequently associated with the salivary glands. HCMV infects between 50% and 80% of adults in the United States (40% worldwide), as indicated by the presence of antibodies in much of the general population. HCMV infection is typically unnoticed in healthy people, but can be life-threatening for the immunocompromised, such as HIV-infected persons, organ transplant recipients, or new born infants. HCMV is the virus most frequently transmitted to a developing fetus. After infection, HCMV has an ability to remain latent within the body for the lifetime of the host, with occasional reactivations from latency. Given the severity and importance of this disease, obtaining an effective vaccine is considered a public health top priority (Sung, H., et al., (2010) Expert review of vaccines 9, 1303-1314; Schleiss, Expert Opin Ther Pat. April 2010; 20(4): 597-602).

The genomes of over 20 different HCMV strains have been sequenced, including those of both laboratory strains and clinical isolates. For example, the following strains of HCMV have been sequenced: Towne (GL239909366), AD169 (Gl:219879600), Toledo (GL290564358) and Merlin (GI: 155573956). HCMV strains AD169, Towne and Merlin can be obtained from the American Type Culture Collection (ATCC VR538, ATCC VR977 and ATCC VR1590, respectively).

Cytomegalovirus contains an unknown number of membrane protein complexes. Of the approximately 30 known glycoproteins in the viral envelope, gH and gL have emerged as particularly interesting due to their presence in several different complexes: dimeric gH/gL, trimeric gH/gL/gO (also known as the gCIII complex), and the pentameric gH/gL/pUL128/pUL130/pUL131 (pUL131 is also referred to as "pUL131A", "pUL131a", or "UL131A"; pUL128, pUL130, and pUL131 subunits sometimes are also referred as UL128, UL130, UL131). CMV is thought to use the pentameric complexes to enter epithelial and endothelial cells by endocytosis and low-pH-dependent fusion but it is thought to enter fibroblasts by direct fusion at the plasma membrane in a process involving gH/gL or possibly gH/gL/gO. The gH/gL and/or gH/gL/gO complex(es) is/are sufficient for fibroblast infection, whereas the pentameric complex is required to infect endothelial and epithelial cells.

The pentameric complex is considered as a major target for CMV vaccination. Viral genes UL128, UL130 and UL131 are needed for endothelial entry (Hahn, Journal of Virology 2004; 78:10023-33). Fibroblast-adapted non-endothelial tropic strains contain mutations in at least one of these three genes. Towne strain, for example, contains a two base pair insertion causing a frame shift in UL130 gene, whereas AD169 contains a one base pair insertion in UL131 gene. Both Towne and AD169 could be adapted for growth in endothelial cells, and in both instances, the frame shift mutations in UL130 or UL131 genes were repaired.

U.S. Pat. No. 7,704,510 discloses that pUL131A is required for epithelial cell tropism. U.S. Pat. No. 7,704,510 also discloses that pUL128 and pUL130 form a complex with gH/gL, which is incorporated into virions. This complex is required to infect endothelial and epithelial cells but not fibroblasts. Anti-CD46 antibodies were found to inhibit HCMV infection of epithelial cells.

CMV vaccines tested in clinical trials include Towne vaccine, Towne-Toledo chimeras, an alpha virus replicon with gB as the antigen, gB/MF59 vaccine, a gB vaccine produced by GlaxoSmithKline, and a DNA vaccine using gB and pp65. pp65 is viral protein that is a potent inducer of CD8+ responses directed against CMV. These vaccines are all poor inducers of antibodies that block viral entry into endothelial/epithelial cells (Adler, S. P. (2013), British Medical Bulletin, 107, 57-68. doi:10.1093/bmb/ldt023).

Preclinical animal studies in CMV vaccines include an inactivated AD169 which has been repaired in the UL131 gene, a DNA vaccine using a wild-type UL130 gene and peptide vaccines using peptides from pUL130 and 131 (Sauer, A, et al., Vaccine 2011; 29:2705-1, doi:10.1016).

CMV gB antigen is considered a poor inducer of antibodies that block entry into endothelial/epithelial cells. In a Phase II clinical trial, the gB/MF59 vaccine was only 50% effective at preventing primary infection among young women with a child at home (Pass, R F, et al., N Engl J Med 2009; 360:1191-9).

Therefore, there is a need for developing CMV vaccines comprising other antigen targets, such as gH/gL, gH/gL/gO, or pentameric complex gH/gL/pUL128/pUL130/pUL131.

SUMMARY OF THE INVENTION

As disclosed and exemplified herein, the inventors discovered that when the cytomegalovirus antigen gL is recombinantly expressed and purified from a mammalian host (such as a CHO cell or a HEK cell), a significant portion of gL is cleaved. To improve the recombinant expression and purification of intact gL protein, mutations were introduced to reduce protease cleavage of gL. The mutants exhibit increased resistance to protease cleavage during recombination production.

Accordingly, in one aspect, the invention provides a recombinant CMV gL protein, or a complex-forming fragment thereof, wherein said gL protein or fragment comprises a mutation at Protease Recognition Site, wherein said mutation reduces protease cleavage at said Protease Recognition Site, as compared to a control. Protease Recognition Site refers to residues 91-102 (numbering based on SEQ ID NO: 1). Preferably, the mutation reduces protease cleavage as compared to a control, without changing the secondary structure of the C-terminal portion of Protease Recognition Site (which is believed to have a β-strand conformation).

Also provided herein are CMV complexes comprising the gL proteins or fragments described herein. Such complexes can be gH/gL complex, gH/gL/gO complex, and pentameric complex gH/gL/pUL128/pUL130/pUL131.

Also provided herein are nucleic acids encoding CMV gL proteins and complex-forming fragments thereof, as described herein. The nucleic acid may be used as a nucleic acid-based vaccine (e.g., a self-replicating RNA molecule encoding the gL or a complex-forming fragment thereof). The nucleic acid may also be used for recombinant production of gL proteins or fragments, or a CMV complex comprising the gL proteins or fragments.

The invention also provides a host cell comprising the nucleic acids described herein. The nucleic acids can be used by the host cell to express a gL protein or a complex-forming fragment thereof, or a CMV complex comprising the gL or complex-forming fragment thereof. Preferably, the CMV complex can be secreted from the host cell. Preferred host cells are mammalian host cells, such as CHO cells or HEK-293 cells.

The invention also provides a cell culture comprising the host cell described herein. Preferably, the culture is at least 20 liters in size. When used for expressing CMV pentameric complex gH/gL/pUL128/pUL130/pUL131, it is preferred that the yield of pentameric complex is at least 0.1 g/L.

The invention also provides a method of inducing an immune response against CMV, comprising administering to a subject in need thereof an immunologically effective amount of the gL protein, or a complex-forming fragment thereof, or a CMV complex comprising the gL protein or fragment, as described herein. The invention also provides a method of inhibiting cytomegalovirus (CMV) entry into a cell, comprising contacting the cell with the gL protein, or a complex-forming fragment thereof, or a CMV complex comprising the gL protein or fragment, as described herein.

Also provided are use of the compositions described herein for inducing an immune response against CMV, and use of the compositions described herein in the manufacture of a medicament for inducing an immune response against CMV.

DETAILED DESCRIPTION OF THE INVENTION

1. Overview

As disclosed and exemplified herein, the inventors discovered that when cytomegalovirus antigen gL is recombinantly expressed and purified from a mammalian host (such as a CHO cell or a HEK cell), a significant portion of gL is cleaved (also referred to as "gL clipping") by an unknown protease. In fact, it was observed that gL clipping occurred during the recombinant expression and purification of three different CMV complexes: gH/gL complex, gH/gL/gO complex, and pentameric complex gH/gL/pUL128/pUL130/pUL131. The clipping of gL caused non-homogeneity of antigen production, and potential loss of neutralizing sites on gL-based antigens.

Figure 1:
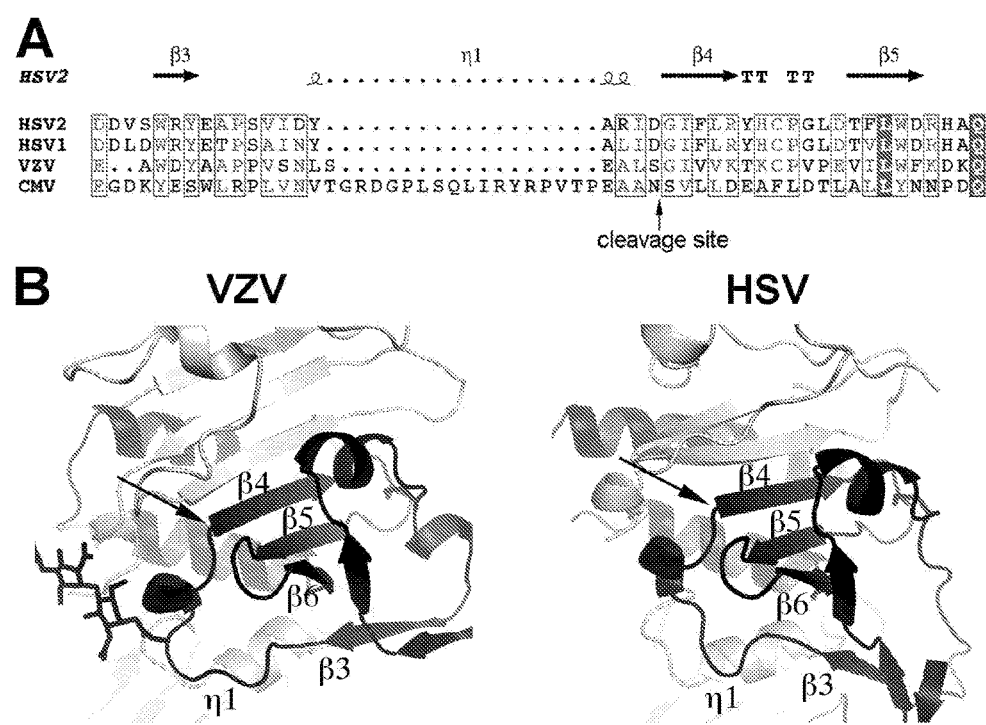
FIG. 1A shows the partial sequence alignment of gL proteins from different herpes viruses near the Protease Recognition Site (SEQ ID NOS 12-15, respectively, in order of appearance).
FIG. 1B shows the secondary structure of gH/gL complex from HSV-2 and VZV. The arrow indicates the cleavage site.

Using western blot and N-terminal sequencing, the inventors identified and mapped the cleavage site to peptide bond between residues 97 and 98 of gL from the Merlin strain (SEQ ID NO:1) (FIG. 1). To solve the clipping problem, the inventors studied the structure features of gL proteins from several related herpes viruses, including HSV1, HSV2, and VZV. The gL proteins from HSV1, HSV2, and VZV do not appear to have clipping problem. Based on the structural studies, the inventors discovered that mutations can be introduced to Protease Recognition Site, comprising amino acid residues 91 and 102, to reduce the protease cleavage of recombinantly expressed gL.

For example, as exemplified herein, A96L/N97S/S98G triple mutation (the "LSG" mutant) and A96I/N97D/S98G triple mutation (the "IDG" mutant) substantially eliminated the gL clipping problem. Two other mutants, deletion of residue Asn97 (delta Asp97), and A96S/N97S/S98T (the "SST" mutant), also showed dramatically decreased gL clipping when gH and gL were co-expressed.

Based on structural analysis of gL proteins from other herpes viruses (FIG. 1), it appears that the Protease Recognition Site adopts, from N-terminus to C-terminus, a possible short α-helix ($^{91}$VTPE$^{94}$) (SEQ ID NO: 27), a short loop ($^{95}$AA$^{96}$), and a conserved β-strand structure ($^{97}$NSV-LLD$^{102}$) (SEQ ID NO: 7). Cleavage occurs at the N-terminal end of the β-strand (FIG. 1). A β-strand is a structural unit of β-sheets in proteins. This is an extended stretch of polypeptide chain typically 3 to 10 amino acids long that forms hydrogen bonds with other β-strands in the same β-sheet. As shown in FIG. 1, this β-strand ((β4 in FIG. 1) together with strands β5 and β6 from gL, as well as β-strands from gH, form a β-sheet. Therefore, in preferred embodiments, the mutation should maintain the secondary structure of the C-terminal portion of the Protease Recognition Site (i.e., the β-strand conformation is preserved, such as the interactions between β4 and other β-strand(s) are substantially maintained). Maintaining the β-strand structure can potentially reduce any negative impact on the assembly of CMV complexes (such as pentameric complexes), and can also potentially preserve important immunogenic epitopes. For example, one or more residues from the Protease Recognition Site can be substituted by a corresponding residue from another herpes virus (such as HSV-1, HSV-2, or VZV). As shown in FIG. 1, sequence and structural analysis shows that substituting a CMV residue with a corresponding HSV-1, HSV-2, or VZV residue does not change the β-strand conformation, while protease cleavage can be reduced. Optionally, the short loop structure immediately preceding the β-strand ($^{95}$AA$^{96}$ in FIG. 1) may also be maintained.

Accordingly, in one aspect, the invention provides a recombinant cytomegalovirus (CMV) gL protein, or a complex-forming fragment thereof, wherein said gL protein or fragment comprises a mutation at Protease Recognition Site, wherein said mutation reduces protease cleavage at said Protease Recognition Site, as compared to a control. Protease Recognition Site refers to residues 91-102 (numbering based on SEQ ID NO:1). Preferably, the mutation reduces protease cleavage as compared to a control, without changing the β-strand structure at the C-terminal portion of the Protease Recognition Site.

Also provided herein are CMV complexes comprising the gL proteins or fragments described herein. Such complexes can be gH/gL complex, gH/gL/gO complex, and pentameric complex gH/gL/pUL128/pUL130/pUL131.

Also provided herein are host cells for recombinant expression of gL proteins or fragments described herein, and CMV complexes comprising gL proteins or fragments described herein. As noted, gL clipping was observed in mammalian host cells during the recombinant production process. Therefore, the mutations disclosed herein are particularly suitable for recombinant production of CMV vaccines in mammalian hosts (which are preferred hosts for many biologics). For example, HEK-293 and CHO cells have long been used for commercial production of biological production. Therefore, incorporating mutations that reduce gL cleavage can improve production efficiency and yield, and reduce the formation of contaminating, partially degraded product.

2. Definitions

The term "complex-forming fragment" of a cytomegalovirus (CMV) protein (such as gL) refers to any part or portion of the protein that retain the ability to form a complex with another CMV protein. Such complexes include, e.g., gH/gL dimeric complex, gH/gL/gO trimeric complex, or gH/gL/pUL128/pUL130/pUL131 pentameric complex. A "pentamer-forming fragment" of a CMV protein (such as gL) refers to any part or portion of the protein that retain the ability to form gH/gL/pUL128/pUL130/pUL131 pentameric complex.

As used herein, "pentameric complex" or "pentamer" refers to a CMV complex that comprises five different subunits: gH, gL, pUL128, pUL130, and pUL131. Although generally referred to as gH/gL/pUL128/pUL130/pUL131 pentamer (or pentameric complex comprising gH, gL, pUL128, pUL130, and pUL131) in the specification, each of the five subunits does not need to be full-length; the term also encompasses pentamers formed by complex-forming fragments of gH, gL, pUL128, pUL130, and pUL131.

The term "mutation" refers to addition, deletion, or substitution of an amino acid residue. The term also includes modifications that introduce a non-naturally occurring amino acid or an amino acid analog into a polypeptide chain.

Charged amino acid residues include: D, E, K, R, and H. Polar, non-charged residues include: S, T, C, Y, N, and Q. Nonpolar or hydrophobic residues include: A, V, L, I, M, W, F, and P.

Amino acid residues comprising a large side chain include: W, F, M, Y, Q, R, E, H, and K. Amino acid residues lack of a side chain or comprising a small side chain include: G, A, V, S, T, C, D, and N.

An amino acid residue comprises a "bulky side chain" when the side chain comprises a branched or cyclic substituent. Examples of amino acid residues with a bulky side chain include tryptophan, tyrosine, phenylalanine, homophenylalanine, leucine, isoleucine, histidine, 1-methyltryptophan, α-methyltyrosine, α-methylphenylalanine, α-methylleucine, α-methylisoleucine, α-methylhistidine, cyclopentylalanine, cyclohexylalanine, naphthylalanine, etc.

Although the present invention is applicable to gL proteins originating from any CMV strain, in order to facilitate its understanding, when referring to amino acid positions in the present specification, the numbering is given in relation to the amino acid sequence of the gL protein of SEQ ID NO:1 originating from the Merlin strain, unless otherwise stated. The present invention is not, however, limited to the Merlin strain. Using the teachings of the present invention, comparable amino acid positions in a gL protein of any other CMV strain can be determined by those of ordinary skill in the art by aligning the amino acid sequences using readily available and well-known alignment algorithms (such as BLAST, using default settings; ClustalW2, using default settings; or algorithm disclosed by Corpet, Nucleic Acids Research, 1998, 16(22):10881-10890, using default parameters). Accordingly, when referring to a "CMV gL protein", it is to be understood as a CMV gL protein from any strain (in addition to Merlin strain). The actual number may have to be adjusted for gL proteins from other strains depending on the actual sequence alignment.

For example, "Protease Recognition Site" is defined as consisting of amino acid residues 91-102 particularly consisting of residues 91, 92, 93, 94, 95, 96, 97, 98, 99, 100, 101 and 102. These numbers are in relation to the amino acid sequence of the gL protein of SEQ ID NO: 1. Protease Recognition Site from gL proteins of other CMV strains, or other gL mutants or variants, or fragments of gL can be ascertained using standard sequence alignment programs that align a query sequence with SEQ ID NO: 1, and identifies residues that match 91-102 of SEQ ID NO: 1.

Specific amino acid residue positions are also numbered according to SEQ ID NO: 1. For example, "S98" refers to position 98 of SEQ ID NO: 1 (which is an S), as well as corresponding residues from other gL sequences (or variants or fragments) that match with S98 of SEQ ID NO: 1, when the sequence is aligned with SEQ ID NO: 1. For simplicity, any residue from a gL sequence (or variant or fragment) that corresponds to S98 of SEQ ID NO: 1 is referred to as S98, although the actual position of that residue may or may not be 98, and the actual residue may or may not be S. For example, a conservative substitution (e.g., T) may be aligned with S98 of SEQ ID NO: 1. A conservative substitution is typically identified as "positive" or "+" by BLAST 2.

Similarly, mutations are also identified according to the numbering of SEQ ID NO: 1. For example, S98G means that any residue from a gL sequence (or variant or fragment) that corresponds to S98 of SEQ ID NO: 1 is mutated to G.

An amino acid residue of a query sequence "corresponds to" a designated position of a reference sequence (e.g., S98 of SEQ ID NO: 1) when, by aligning the query amino acid sequence with the reference sequence, the position of the residue matches the designated position. Such alignments can be done by hand or by using well-known sequence alignment programs such as ClustalW2, or "BLAST 2 Sequences" using default parameters.

An " " refers to a sequence that is at least 10 amino acid residues long, and is at least 50% identical to SEQ ID NO: 5. As shown in FIG. 1, for wild type gL from Merlin strain, a 17-residue fragment unique to CMV gL, as compared to HSV1, HSV2, and VZV, has been identified (shown as "η1"). Preferably, the Insert Region comprises at least 11, at least 12, at least 13, at least 14, at least 15, at least 16, at least 17, at least 18, at least 19, or at least 20 residues, and/or is at least 60%, at least 65%, at least 70%, at least 75%, at least 80%, at least 85%, at least 90%, at least 95%, or 100% identical to SEQ ID NO: 5. In certain embodiments, the Insert Region comprises a sequence in which one to eight amino acid residues of SEQ ID NO: 5 are conservatively substituted.

"Conservatively substituted" means that a residue is replaced by another, biologically similar residue. Examples include substitution of amino acid residues with similar characteristics, e.g. small amino acids, acidic amino acids, polar amino acids, basic amino acids, hydrophobic amino acids and aromatic amino acids. An example of conservative amino acid substitutions includes those in the following Table 1, and analogous substitutions of the original residue by non-natural alpha amino acids which have similar characteristics.

Typically, the N-terminal signal sequence of gL proteins is cleaved by a host cell signal peptidase to produce mature gL proteins. The gL proteins in HCMV membrane complexes of the invention may lack an N-terminal signal sequences. An example of gL protein lacking N-terminal signal sequences is SEQ ID NO: 4, which lacks an N-terminal signal sequence and consists of amino acid residues 31-278 of SEQ ID NO: 1.

TABLE 1

| Original Residue | Very Highly - Conserved Substitutions | Highly Conserved Substitutions (from the Blosum90 Matrix) | Conserved Substitutions (from the Blosum65 Matrix) |
| --- | --- | --- | --- |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

Unless otherwise specified, the percent identity of two sequences is determined over the entire length of the shorter of the two sequences.

3. Modified Cmv GL Proteins and Complexes

A. Modified gL Proteins

In one aspect, the invention provides a modified CMV gL protein, or a complex-forming fragment thereof, that reduces clipping (cleavage) at the peptide bond between residues N97 and S98.

Human CMV glycoprotein L (gL) is encoded by the UL115 gene. gL is thought to be essential for viral replication and all known functional properties of gL are directly associated with its dimerization with gH. The gH/gL complex is required for the fusion of viral and plasma membranes leading to virus entry into the host cell. gL from HCMV strain Merlin (GI:39842115, SEQ ID NO: 1) and HCMV strain Towne (GI:239909463, SEQ ID NO: 2) have been reported to be 278 amino acids in length. gL from HCMV strain AD169 (GI:2506510, SEQ ID NO: 3) has been reported to be 278 amino acids in length, include a signal sequence at its N-terminus (amino acid residues 1-35), have two N-glycosylation sites (at residues 74 and 114) and lack a TM domain (Rigoutsos, I, et al., Journal of Virology 77 (2003): 4326-44). The N-terminal signal sequence in SEQ ID NO: 1 is predicted to comprise amino acid residues 1-30. SEQ ID NO: 2 shares 98% amino acid identity with SEQ ID NO: 1. Sequencing of the full-length gL gene from 22 to 39 clinical isolates, as well as laboratory strains AD169, Towne and Toledo revealed less than 2% variation in the amino acid sequences among the isolates (Rasmussen, L, et al., Journal of Virology 76 (2002): 10841-10888).

While gL is thought to be essential for viral replication, all known functional properties of gL are directly associated with its dimerization with gH.

gL proteins of the invention can be gL variants that have various degrees of identity to SEQ ID NO: 1 such as at least 60%, 70%, 80%, 85%, 90%, 91%, 92%, 93%, 94%, 95%, 96%, 97%, 98% or 99% identical to the sequence recited in SEQ ID NO: 1, SEQ ID NO: 2, or SEQ ID NO: 3. gL proteins of the invention can have various degrees of identity to SEQ ID NO: 4 such as at least 60%, 70%, 80%, 85%, 90%, 91%, 92%, 93%, 94%, 95%, 96%, 97%, 98% or 99% identical to the sequence recited in SEQ ID NO: 4. In certain embodiments, the gL variant proteins: (i) form part of the dimeric complex gH/gL; (ii) form part of the trimeric gH/gL/gO complex; (iii) form part of the pentameric gH/gL/pUL128/pUL130/pUL131 complex; (iv) comprise at least one epitope from SEQ ID NO: 1, SEQ ID NO: 2, SEQ ID NO: 3, or SEQ ID NO: 4; and/or (v) can elicit antibodies in vivo which immunologically cross react with a CMV virion.

Also encompassed in the invention are complex-forming fragments of gL proteins described herein. A complex-forming fragment of gL can be any part or portion of the gL protein that retains the ability to form a complex with another CMV protein. In certain embodiments, a complex-forming fragment of gL forms part of the dimeric complex gH/gL. In certain embodiments, a complex-forming fragment of gL forms part of the trimeric gH/gL/gO complex. In certain embodiments, a complex-forming fragment of gL forms part of the pentameric gH/gL/pUL128/pUL130/pUL131 complex. A complex-forming fragment of gL can be obtained or determined by standard assays known in the art, such as co-immunoprecipitation assay, cross-linking, or co-localization by fluorescent staining, etc. In certain embodiments, the complex-forming fragment of gL also (i) comprises at least one epitope from SEQ ID NO: 1, SEQ ID NO: 2, SEQ ID NO: 3, or SEQ ID NO: 4; and/or (ii) can elicit antibodies in vivo which immunologically cross react with a CMV virion.

In certain embodiments, the gL protein described herein, or a complex-forming fragment thereof, comprises a mutation at Protease Recognition Site (residues 91-102), wherein said mutation reduces protease cleavage at said Protease Recognition Site, as compared to a control.

A variety of controls may be used. The level of protease cleavage (at peptide bond between residues 97 and 98) of a corresponding wild type gL under substantially the same condition can be used as a control. Alternatively, a control may be a pre-determined level or a threshold level (e.g., 20%, 25%, or 30% of the total gL protein). The percentage refers to molar percentage.

For example, the mutation can result in a reduction in protease cleavage at the peptide bond between residues 97 and 98 by at least 10%, at least 20%, at least 30%, at least 40%, at least 50%, at least 60%, at least 65%, at least 70%, at least 75%, at least 80%, at least 85%, at least 90%, or at least 95% etc., as compared to that of wild type, when recombinantly expressed in a mammalian host cell under a standard culturing condition for that host cell.

Alternatively or in addition, the protease cleavage is reduced by at least 3 fold, at least 5 fold, at least 10 fold, at least 20 fold, at least 30 fold, at least 40 fold, at least 50 fold, at least 60 fold, at least 70 fold, at least 75 fold, at least 80 fold, at least 90 fold or at least 100 fold, as compared to that of wild type, when recombinantly expressed in a mammalian host cell under a standard culturing condition for that host cell.

Alternatively or in addition, the mutation can be one wherein no more than about 35% of the gL molecules, or complex-forming fragment thereof, are cleaved at a peptide bond between residues 97 and 98, when recombinantly expressed in a mammalian host cell under a standard culturing condition for that host cell. For example, the mutation can result in no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1% of the gL molecules, or complex-forming fragment thereof, are cleaved at peptide bond between residues 97 and 98, when recombinantly expressed in a mammalian host cell under a standard culturing condition for that host cell. The percentage refers to molar percentage.

Standard culturing conditions for commonly used mammalian host cells are known. For example, for a CHO cell, a standard culturing condition can be temperature at 36.5° C. in a pH 7.0 medium, with ≤10%, $CO_2$. In one specific example, Expi293 cells were transfected to express pentameric complex (gH/gL/pUL128/pUL130/pUL131) at 37° C. and in pH 7.0 under 8% $CO_2$ for three days, and supernatants of the cell culture were affinity purified and analyzed with western blots, as shown in examples below.

The mutation comprises addition, deletion, substitution, or a combination thereof, of an amino acid residue. Preferably, the mutation substantially preserves the secondary structure of the C-terminal portion of the Protease Recognition Site. In particular, as shown in FIG. 1, residues of the C-terminal portion of said Protease Recognition Site form a β-strand, which is believed to interact with other β-strands to form a β-sheet. Preferably, said mutation maintains this β-strand conformation. Potential advantages of maintaining the secondary structure include, e.g., facilitating the assembly of gL-containing complexes (e.g., gH/gL, gH/gL/gO, or gH/gL/pIL128/pUL130/pUL131), and maintaining key immunogenic epitopes. Optionally, the short loop structure immediately preceding the β-strand is also preserved.

Many computer programs and algorithms are available to predict secondary structure, including I-TASSER, HHpred, RaptorX, MODELLER, SWISS-MODEL, Robetta Beta, SPARKSx, PEP-FOLD, Phyre and Phyre2, RAPTOR, QUARK, Abalone, Foldit, etc. Whether a mutation changes the secondary structure of the Protease Recognition Site can be analyzed using these tools.

In certain embodiments, the mutation comprises addition of one or more amino acid residues. For example, the mutation can comprise addition of two to five amino acid residues. In certain embodiments, the two to five amino acid residues comprise both polar residue(s) and non-polar residue(s).

In certain embodiments, the mutation comprises the addition of one or more residues between residues N97 and S98. As shown in the Examples, the peptide bond between N97 and S98 is cleaved by a protease; therefore, introducing one or more additional residues between N97 and S98 can result in a mutant gL (or fragment) that is more cleavage resistant. In an exemplary embodiment, the mutation comprises addition of F, Q, or a combination thereof, between residues 97 and 98. In an exemplary embodiment, the mutation comprises addition of FQ or QF between residues 97 and 98.

In certain embodiments, the mutation comprises deletion of one or more amino acid residues, such as deletion of one to three amino acid residues. In certain embodiments, the mutation comprises the deletion of at least one residue selected from the group consisting of: V91, T92, P93, E94, A95, A96, N97, S98, V99, L100, L101, D102, and a combination thereof. In certain embodiments, the mutation comprises deletion of at least one residue selected from the group consisting of: E94, A95, A96, N97, S98, V99, L100, L101, D102 and a combination thereof. In an exemplary embodiment, the mutation comprises deletion of at least one residue selected from the group consisting of: A96, N97, S98, and a combination thereof. In an exemplary embodiment, the mutation comprises deleting N97.

In certain embodiments, the mutation comprises substituting a residue with a corresponding residue from the gL protein of another herpes virus. Herpes virus (Herpesviridae) family include, e.g., herpes simplex viruses 1 and 2 (HSV-1 or HHV-1, HSV-2 or HHV-2), varicella-zoster virus (VZV or HHV-3), Epstein-Barr virus (EBV or HHV-4), human herpesvirus 6 (HHV-6), human herpesvirus 7 (HHV-7), and Kaposi's sarcoma-associated herpesvirus (HHV-8). In certain embodiments, the gL protein from another herpes virus is the gL protein from HSV1, HSV2, VZV, EBV, PrV, or bovine herpesvirus 5.

One potential advantage of substituting a CMV residue with a corresponding residue from another herpes virus is that the secondary structure of the Protease Recognition Site will likely be preserved. As shown in FIG. 1, HSV-1, HSV-2 and VZV all share substantially the same secondary structure, especially, the C-terminal portion of the Protease Recognition Sites all adopt a β-stand structure.

If multiple substitutions are made, they do not have to come from the same herpes virus. For example, one may substitute a first CMV residue with the corresponding residue from HSV-1, a second residue with the corresponding residue from HSV-2, and/or a third CMV residue with the corresponding residue from VZV, etc. Therefore, the mutation may comprises a first amino acid residue substituted with a corresponding residue from a first other herpes virus gL protein, and a second amino acid residue substituted with a corresponding residue from a second other herpes virus gL protein, and/or a third amino acid residue substituted with a corresponding residue from a third other herpes virus gL protein, etc.

In certain embodiments, the mutation comprises substituting E94 with A.

In certain embodiments, the mutation comprises substituting A95 with R, L, or N.

In certain embodiments, the mutation comprises substituting A96 with a non-polar residue or with a residue that comprises a large side chain, such as W, F, or M. In certain embodiments, the mutation comprises substituting A96 with I, L, or S.

In certain embodiments, the mutation comprises substituting N97 with a polar residue or a non-polar residue. The polar residue can comprise a small side chain or a large side chain. In certain embodiments, the mutation comprises substituting N97 with S, D, E, A, or Y.

In certain embodiments, the mutation comprises substituting S98 with an amino acid residue with a small side chain, such as G, A, V, S, T, C, D, or N. In certain embodiments, the mutation comprises substituting S98 with G, T, V, or I.

In certain embodiments, the mutation comprises substituting V99 with an amino acid residue with I.

In certain embodiments, the mutation comprises substituting L100 with an amino acid residue with F or V.

In certain embodiments, the mutation comprises substituting L101 with an amino acid residue with V.

The addition, deletion, and substitutions described herein can be used in singular, or in any combination. For example, the gL mutant may comprise an addition at one position, a deletion at a second position, and a substitution at a third position.

In certain embodiments, the gL protein or fragment comprises an Insert Region at the N-terminus of the Protease Recognition Site. As shown in FIG. 1, as compared to gL proteins from HSV-1, HSV-2, and ZVZ, the CMV gL protein comprises an extra 17-residue insert. As shown in the Examples, when this 17-residue insert was partially or fully deleted, the gL protein became more prone to protease cleavage. Therefore, the 17-residue insert appears to at least partially block the access of the protease to the Protease Recognition Site. Therefore, maintaining an Insert Region at the N-terminus of the Protease Recognition Site may be desirable. An "Insert Region" should be at least 10 amino acid residues long, and is at least 50% identical to SEQ ID NO: 5 (which is the original 17-residue fragment unique to CMV gL, as compared to HSV1, HSV2, and VZV).

In certain embodiments, the mutation comprises introducing a non-naturally occurring amino acid residue, which is believed to reduce the protease cleavage.

In certain embodiments, the mutation comprises introducing an amino acid residue comprising a bulky side chain, which is believed to at least partially block the access of the protease to the Protease Recognition Site, and reduces protease cleavage.

B. CMV Protein Complexes

In another aspect, the invention provides a complex comprising the modified CMV gL protein, or a complex-forming fragment thereof, described herein. Such complexes include, e.g., (i) isolated dimeric complexes comprising: the modified gL protein, or a complex-forming fragment thereof, described herein, and CMV proteins gH or a complex-forming fragment thereof; (ii) isolated trimeric complex comprising the modified gL protein, or a complex-forming fragment thereof, described herein, and CMV proteins gH or a complex-forming fragment thereof, and gO or a complex-forming fragment thereof; and (iii) isolated pentameric complexes comprising the modified gL protein, or a complex-forming fragment thereof, described herein, and CMV proteins pUL128 or a complex-forming fragment thereof, pUL130 or a complex-forming fragment thereof, pUL131 or a complex-forming fragment thereof, and gH or a complex-forming fragment thereof. Also included are any other complexes comprising gL (or a complex-forming fragment thereof) as a component.

Although gH, gL, gO, pUL128, pUL130, pUL131 may be referred to as glycoproteins, this nomenclature should not be taken to mean that these proteins must be glycosylated when used with the invention. On the contrary, in some embodiments of the invention, one or more of polypeptides are not glycosylated. Usually, however, one or more (or all) polypeptides in a complex of the invention are glycosylated. In some embodiments, one or more (or all) polypeptides in a complex of the invention are glycosylated by glycosylation mutants of cultured cells, such as mutated mammalian cells. Such glycosylation mutants produce a pattern of polypeptide glycosylation which differs from a wild-type pattern of glycosylation, i.e. the resulting polypeptide glycoforms differ from wild-type glycoforms.

In certain embodiments, the glycosylation pattern of the gL (or a complex-forming fragment thereof), or a complex comprising gL (or a complex-forming fragment thereof) has a mammalian glycosylation pattern; and/or does not have an insect cell pattern of glycosylation. In some embodiments, one or more of the proteins of the complex contain complex N-linked side chains with a penultimate galactose and terminal sialic acid.

For recombinant production of protein complexes (such as pentameric complex), it may be desirable that the complex is soluble. Based on sequence analysis, CMV gH protein comprises a transmembrane (TM) domain, but gL, gO, pUL128, pUL130, and pUL131 do not have transmembrane domains. So, to produce a soluble complex (e.g., pentameric complex), the gH subunit of the pentameric complex may lack the TM domain. For example, a gH fragment comprising the N-terminal signal sequence and the ectodomain, but not the TM domain, of gH can be used.

The gH from CMV strain Towne is shown as SEQ ID NO: 6 (GI:138314, 742 amino acid residues). gH from Towne has been characterized as having: (i) six N-glycosylation sites (at residues 55, 62, 67, 192, 641 and 700); (ii) a hydrophobic signal sequence at its N-terminus (amino acid residues 1-23); (iii) an ectodomain (residues 24-717) that projects out of the cell into the extracellular space; (iv) a hydrophobic transmembrane (TM) domain (residues 718-736); and (v) a C-terminal cytoplasmic domain (residues 737-742). The TM domains of gH proteins from other strains, or of other gH variants and fragments, can be identified according to sequence alignment.

For ease of production, the recombinantly produced CMV complex (such as pentameric complex) may be secreted from the host cell into culturing medium.

In certain embodiments, said pentameric complex is secreted from the host cell. It has been reported that the presence of all five subunits, gH, gL, pUL128, pUL131, and pUL131, is sufficient for the assembly of the pentameric complex in ER before it is exported to the Golgi apparatus. See, Ryckman et al., J Virol. January 2008; 82(1): 60-70.

Alternatively or in addition, an appropriate signal peptide may be used in one or more of the five subunits (e.g., by making a fusion protein with a secretory signal). Signal sequences (and expression cassette) for producing secretory proteins are known in the prior art. In general, leader peptides are 5-30 amino acids long, and are typically present at the N-terminus of a newly synthesized protein. The core of the signal peptide generally contains a long stretch of hydrophobic amino acids that has a tendency to form a single alpha-helix. In addition, many signal peptides begin with a short positively charged stretch of amino acids, which may help to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein.

C. Nucleic Acid Encoding Modified gL Proteins and Complexes

In another aspect, the invention provides a nucleic acid comprising a sequence that encodes the modified gL protein, or a complex-forming fragment thereof, described herein. The nucleic acid can be DNA or RNA.

In certain embodiments, the nucleic acid is DNA. DNA-based expression systems for expression and purification of recombinant proteins are well-known in the art. For example, the expression system may be a vector comprising a nucleotide sequence that encodes the modified gL or gL fragment described herein, which is operably linked to an expression control sequence that regulates the expression of the modified gL or gL fragment in a host cell, such as a mammalian host cell, a bacterial host cell, or an insect host cell. The expression control sequence may be a promoter, an enhancer, a ribosome entry site, or a polyadenylation sequence, for example. Other expression control sequences contemplated for use in the invention include introns and 3' UTR sequences.

The recombinantly expressed modified gL protein of fragment thereof, or a complex comprising the modified gL protein or fragment thereof can be purified using methods described herein, such as purification methods disclosed in WO 2014/005959, or other methods known in the art.

In certain embodiments, the nucleic acid molecule is a vector derived from an adenovirus, an adeno-associated virus, a lentivirus, or an alphavirus. In certain embodiments, the nucleic acid molecule is a replication-deficient viral vector.

In certain embodiments, the nucleic acid is RNA. In certain embodiments, the nucleic acid is a self-replicating RNA molecule, such as an alphavirus-derived RNA replicon.

Self-replicating RNA molecules are well known in the art and can be produced by using replication elements derived from, e.g., alphaviruses, and substituting the structural viral proteins with a nucleotide sequence encoding a protein of interest. A self-replicating RNA molecule is typically a plus-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded antigen, or may be transcribed to provide further transcripts with the same sense as the delivered RNA which are translated to provide in situ expression of the antigen. The overall result of this sequence of transcriptions is a huge amplification in the number of the introduced replicon RNAs and so the encoded antigen becomes a major polypeptide product of the cells. Cells transfected with self-replicating RNA briefly produce antigen before undergoing apoptotic death. This death is a likely result of requisite double-stranded (ds) RNA intermediates, which also have been shown to super-activate dendritic cells. Thus, the enhanced immunogenicity of self-replicating RNA may be a result of the production of pro-inflammatory dsRNA, which mimics an RNA-virus infection of host cells.

One suitable system for achieving self-replication in this manner is to use an alphavirus-based replicon. Alphaviruses comprise a set of genetically, structurally, and serologically related arthropod-borne viruses of the Togaviridae family. Twenty-six known viruses and virus subtypes have been classified within the alphavirus genus, including, Sindbis virus, Semliki Forest virus, Ross River virus, and Venezuelan equine encephalitis virus. As such, the self-replicating RNA of the invention may incorporate a RNA replicase derived from semliki forest virus (SFV), sindbis virus (SIN), Venezuelan equine encephalitis virus (VEE), Ross-River virus (RRV), eastern equine encephalitis virus, or other viruses belonging to the alphavirus family.

An alphavirus-based "replicon" expression vectors can be used in the invention. Replicon vectors may be utilized in several formats, including DNA, RNA, and recombinant replicon particles. Such replicon vectors have been derived from alphaviruses that include, for example, Sindbis virus (Xiong et al. (1989) Science 243:1188-1191; Dubensky et al., (1996) J. Virol. 70:508-519; Hariharan et al. (1998) J. Virol. 72:950-958; Polo et al. (1999) PNAS 96:4598-4603), Semliki Forest virus (Liljestrom (1991) Bio/Technology 9:1356-1361; Berglund et al. (1998) Nat. Biotech. 16:562-565), and Venezuelan equine encephalitis virus (Pushko et al. (1997) Virology 239:389-401). Alphaviruses-derived replicons are generally quite similar in overall characteristics (e.g., structure, replication), individual alphaviruses may exhibit some particular property (e.g., receptor binding, interferon sensitivity, and disease profile) that is unique. Therefore, chimeric alphavirus replicons made from divergent virus families may also be useful.

In some embodiments, CMV gL proteins (or fragments thereof) described herein are delivered using alphavirus replicon particles (VRP). An "alphavirus replicon particle" (VRP) or "replicon particle" is an alphavirus replicon packaged with alphavirus structural proteins.

Uses of alphavirus-based RNA replicon are known in the art, see, e.g., WO 2013006837, paragraphs [0155] to [0179]. The RNA replicon can be administered without the need for purification of the protein encoded therein.

In certain embodiments, the nucleic acid molecule is part of a vector derived from an adenovirus. The adenovirus genome is a linear double-stranded DNA molecule of approximately 36,000 base pairs with the 55-kDa terminal protein covalently bound to the 5' terminus of each strand. Adenoviral ("Ad") DNA contains identical Inverted Terminal Repeats ("ITRs") of about 100 base pairs with the exact length depending on the serotype. The viral origins of replication are located within the ITRs exactly at the genome ends. Adenoviral vectors for use with the present invention may be derived from any of the various adenoviral serotypes, including, without limitation, any of the over 40 serotype strains of adenovirus, such as serotypes 2, 5, 12, 40, and 41.

In certain embodiments, the nucleic acid molecule is part of a vector derived from an Adeno Associated Virus (AAV). The AAV genome is a linear single-stranded DNA molecule containing approximately 4681 nucleotides. The AAV genome generally comprises an internal nonrepeating genome flanked on each end by inverted terminal repeats (ITRs). The ITRs are approximately 145 base pairs (bp) in length. The ITRs have multiple functions, including serving as origins of DNA replication and as packaging signals for the viral genome. AAV is a helper-dependent virus; that is, it requires co-infection with a helper virus (e.g., adenovirus, herpesvirus or vaccinia) in order to form AAV virions in the wild. In the absence of co-infection with a helper virus, AAV establishes a latent state in which the viral genome inserts into a host cell chromosome, but infectious virions are not produced. Subsequent infection by a helper virus rescues the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus.

In certain embodiments, the nucleic acid molecule is part of a vector derived from a retroviruses. A selected gene can be inserted into a vector and packaged in retroviral particles using techniques known in the art. The recombinant virus can then be isolated and delivered to cells of the subject either in vivo or ex vivo. A number of retroviral systems have been described. See, e.g., U.S. Pat. No. 5,219,740; Miller and Rosman (1989) BioTechniques 7:980-90; Miller, A. D. (1990) Human Gene Therapy 1:5-14; Scarpa et al. (1991) Virology 180:849-52; Burns et al. (1993) Proc. Natl. Acad. Sci. USA 90:8033-37; Boris-Lawrie and Temin (1993) Curr. Opin. Genet. Develop. 3: 102-09.

The invention also provides host cells comprising the nucleic acid molecules disclosed herein. Host cells suitable for harboring the nucleic acid molecules and/or for expressing recombinant proteins, and methods of introducing a nucleic acid into a suitable host cell, are known in the art.

4. Recombinant Production of GL Proteins and Complexes

The invention also provides a host cell comprising the nucleic acids encoding the gL protein and fragment thereof, as described above.

Preferably, the host cells are mammalian cells (e.g., human, non-human primate, horse, cow, sheep, dog, cat, and rodent (e.g., hamster), avian cells (e.g., chicken, duck, and geese). Suitable mammalian cells include, for example, Chinese hamster ovary (CHO) cells, human embryonic kidney cells (HEK-293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like.

In certain embodiments, the host cell is a HEK-293 cell. In certain embodiments, the host cell is a CHO cell. In certain embodiments, the polynucleotide encoding the gL protein (or fragment thereof) described herein is integrated into the genomic DNA of the CHO cell. For recombinant production of a CMV protein complex, the nucleotide sequence encoding other subunits of the complex should also be integrated into the genomic DNA of the CHO cell.

Accordingly, in certain embodiments, the host cell comprises one or more polynucleotide sequences encoding CMV pentameric complex, said pentameric complex comprising: gH or a pentamer-forming fragment thereof, gL or a pentamer-forming fragment thereof, pUL128 or a pentamer-forming fragment thereof, pUL130 or a pentamer-forming fragment thereof, and pUL131 or a pentamer-forming fragment thereof. In certain embodiments, the one or more polynucleotide sequences encoding CMV pentameric complex are integrated into the genomic DNA of said host cell. In certain embodiments, the host cell, when cultured under a suitable condition, expresses said CMV pentameric complex (which is preferably soluble and/or secreted from the host cell).

Exemplary CHO cell lines available at European Collection of Cell Cultures (ECACC) are listed in Table 2. Any CHO cells listed in Table 2 may be used.

TABLE 2

| Cell Line Name | Keywords |
| --- | --- |
| CHO | Hamster Chinese ovary |
| CHO (PROTEIN FREE) | Chinese hamster ovary |
| CHO-CHRM1 | Human cholinergic receptor muscarinic M1, CHRM1, G Protein Coupled Receptor, GPCR, Transfected, InSCREENeX SCREENflexTM, CHO-K1 Host. |
| CHO-CHRM2 | Human cholinergic receptor muscarinic M2, CHRM2, G Protein Coupled Receptor, GPCR, Transfected, InSCREENeX SCREENflexTM, CHO-K1 Host. |
| CHO-CHRM5 | Human cholinergic receptor muscarinic M5, CHRM5, G Protein Coupled Receptor, GPCR, Transfected, InSCREENeX SCREENflexTM, CHO-K1 Host. |
| CHO-CNR1 | Human cannabinoid receptor I, CNR1 Gene ID 1268, G Protein Coupled Receptor, GPCR, Transfected, InSCREENeX SCREENflexTM, CHO-K1 Host |
| CHO-FFAR2 | Human free fatty acid receptor 2, FFAR2, G Protein Coupled Receptor, GPCR, Transfected, InSCREENeX SCREENflexTM, CHO-K1 Host. |
| CHO-GPR120 | Human receptor GPR120 (orphan), GPR120, G Protein Coupled Receptor, GPCR, Transfected, InSCREENeX SCREENflexTM, CHO-K1 Host. |
| CHO-K1 | Hamster Chinese ovary |
| CHO-K1-AC-free | Hamster Chinese Ovary, serum-free |
| CHO-K1/SF | Hamster Chinese ovary (MEM adapted) |
| CHO-NPY1R | Human neuropeptide Y receptor, NPY1R, Gene ID 4886, G Protein Coupled Receptor, GPCR, Transfected, InSCREENeX SCREENflexTM, CHO-K1 Host. |

TABLE 2-continued

| Cell Line Name | Keywords |
| --- | --- |
| CHO-OPRL1 | Human opiate receptor-like 1, OPRL1, G Protein Coupled Receptor, GPCR, Transfected, InSCREENeX SCREENflexTM, CHO-K1 Host. |
| CHO-SSTR1 | Human Somatostatin Receptor 1, SSTR1 G Protein Coupled Receptor, GPCR, Transfected, InSCREENeX SCREENflexTM, CHO-K1 Host. |
| CHO/dhFr- | Hamster Chinese ovary |
| CHO/dhFr-AC-free | Hamster Chinese Ovary, serum-free |
| RR-CHOKI | Hamster Chinese ovary |
| T02J-10/10 (CHO-GCGR (GCGR)) | Human glucagon receptor, GCGR, G Protein Coupled Receptor, GPCR, Transfected, InSCREENeX SCREENflex ™, CHO-K1 Host. |

Various CHO cell lines are also available from American Type Culture Collection (ATCC), such as CHO cell lines hCBE11 (ATCC® PTA-3357™), E77.4 (ATCC® PTA-3765™), hLT-B: R-hG1 CHO #14 (ATCC® CRL-11965™), MOR-CHO-MORAb-003-RCB (ATCC® PTA-7552™), AQ.C2 clone 11B (ATCC® PTA-3274™), AQ.C2 clone 11B (ATCC® PTA-3274™), hsAQC2 in CHO-DG44 (ATCC® PTA-3356™), xrs5 (ATCC® CRL-2348™), CHO-K1 (ATCC® CCL-61 ™), Lec1 [originally named Pro-5WgaRI3C] (ATCC® CRL-1735™), Pro-5 (ATCC® CRL-1781 ™), ACY1-E (ATCC® 65421™) ACY1-E (ATCC® 65420™), pgsE-606 (ATCC® CRL-2246™), CHO-CD36 (ATCC® CRL-2092™), pgsC-605 (ATCC® CRL-2245™), MC2/3 (ATCC® CRL-2143™), CHO-ICAM-1 (ATCC® CRL-2093™), and pgsB-618 (ATCC® CRL-2241 ™). Any one of these CHO cell lines may be used.

Other commercially available CHO cell lines include, e.g., FreeStyle™ CHO-S Cells and Flp-In™-CHO Cell Line from Life Technologies.

Other suitable host cells include, e.g., a CHO cell in which the expression level or activity of C12orf35 protein is reduced, as compared to a control (see, e.g., WO2015/092735, incorporated herein by reference, which provides a detailed description of mammalian cells wherein the expression level or activity of C12orf35 protein is reduced as compared to a control), a CHO cell in which the expression level or activity of FAM60A protein is reduced, as compared to a control (see, e.g., WO2015/092737, incorporated herein by reference, which provides a detailed description of mammalian cells wherein the expression level or activity of FAM60A protein is reduced); a CHO cell in which the expression level or activity of matriptase is reduced, as compared to a control (U.S. Provisional Patent application No. 61/985,589, filed Apr. 29, 2014 and incorporated herein by reference, and U.S. Provisional Patent Application No. 61/994,310, filed May 16, 2014 and incorporated herein by reference, provides a detailed description of mammalian cells wherein the expression level or activity of matriptase is reduced).

Methods for expressing recombinant proteins in CHO cells in general have been disclosed. See, e.g., in U.S. Pat. No. 4,816,567 and U.S. Pat. No. 5,981,214.

EP patent application EP14191385.5 filed Oct. 31, 2014 (incorporated herein by reference) discloses mammalian host cells, in particular CHO cells, in which the sequence(s) encoding CMV proteins gH, gL, pUL128, pUL130, pUL131 (or a complex-forming fragment thereof) are stably integrated into the genome.

Also provided herein is a cell culture comprising the host cell described herein. The cell culture can be large scale, e.g., at least about 10 L, at least about 20 L, at least about 30 L, at least about 40 L, at least about 50 L, at least about 60 L, at least about 70 L, at least about 80 L, at least about 90 L, at least about 100 L, at least about 150 L, at least about 200 L, at least about 250 L, at least about 300 L, at least about 400 L, at least about 500 L, at least about 600 L, at least about 700 L, at least about 800 L, at least about 900 L, at least about 1000 L, at least about 2000 L, at least about 3000 L, at least about 4000 L, at least about 5000 L, at least about 6000 L, at least about 10,000 L, at least about 15,000 L, at least about 20,000 L, at least about 25,000 L, at least about 30,000 L, at least about 35,000 L, at least about 40,000 L, at least about 45,000 L, at least about 50,000 L, at least about 55,000 L, at least about 60,000 L, at least about 65,000 L, at least about 70,000 L, at least about 75,000 L, at least about 80,000 L, at least about 85,000 L, at least about 90,000 L, at least about 95,000 L, at least about 100,000 L, etc.

In certain embodiments, the yield of CMV complex (such as pentameric complex) is at least about 0.01 g/L, at least about 0.02 g/L, at least about 0.03 g/L, at least about 0.05 g/L, at least about 0.06 g/L, at least about 0.07 g/L, at least about 0.08 g/L, at least about 0.09 g/L, at least about 0.1 g/L, at least about 0.15 g/L, at least about 0.20 g/L, at least about 0.25 g/L, at least about 0.3 g/L, at least about 0.35 g/L, at least about 0.4 g/L, at least about 0.45 g/L, at least about 0.5 g/L, at least about 0.55 g/L, at least about 0.6 g/L, at least about 0.65 g/L, at least about 0.7 g/L, at least about 0.75 g/L, at least about 0.8 g/L, at least about 0.85 g/L, at least about 0.9 g/L, at least about 0.95 g/L, or at least about 1.0 g/L.

Also provided herein is a process of producing cytomegalovirus (CMV) gL protein, or a fragment thereof, or a complex comprising said gL protein or fragment, comprising: (i) culturing the host cell described herein under a suitable condition, thereby expressing said gL protein, or fragment thereof; and (ii) harvesting said gL protein, or fragment thereof, or the complex comprising said gL protein or fragment, from the culture.

In certain embodiments, the gL protein (or fragment thereof), or complex comprising a complex comprising said gL protein or fragment described herein is purified. The gL protein (or fragment thereof) can be purified using any suitable methods, such as HPLC, various types of chromatography (such as hydrophobic interaction, ion exchange, affinity, chelating, and size exclusion), electrophoresis, density gradient centrifugation, solvent extraction, or the like.

For example, ion exchange may be used to purify the gL protein (or fragment thereof), or complex comprising a complex comprising said gL protein or fragment. Examples of materials useful in the ion exchange chromatography include DEAE-cellulose, QAE-cellulose, DEAE-cephalose, QAE-cephalose, DEAE-Toyopearl, QAE-Toyopearl, Mono Q, Mono S, Q sepharose, SP sepharose, etc. In one exemplary embodiment, the method uses a Mono S column. In another exemplary embodiment, the method uses a Mono Q column.

Alternatively or in addition, affinity-based purification may be used. Examples of affinity-purification tags include, e.g., His tag (binds to metal ion), an antibody (binds to protein A or protein G), maltose-binding protein (MBP) (binds to amylose), glutathione-S-transferase (GST) (binds to glutathione), FLAG tag (Asp-Tyr-Lys-Asp-Asp-Asp-Asp-Lys) (SEQ ID NO: 8) (binds to an anti-flag antibody), Strep tag (binds to streptavidin or a derivative thereof).

One exemplary embodiment is Strep tag (or streptavidin affinity tag), a tag that binds to streptavidin or a derivative thereof, such as Strep-Tactin. Strep tag comprises a peptide of nine amino acids: Ala-Trp-Arg-His-Pro-Gln-Phe-Gly-Gly (SEQ ID NO: 9), or eight amino acids (also called strep-tag II): Trp-Ser-His-Pro-Gln-Phe-Glu-Lys (SEQ ID NO: 10). Elution of a protein attached to a strep-tag from the column can be performed using biotin or a derivative or homologue thereof, such as desthio-biotin.

The affinity-purification tag may be attached by any suitable means, and may be attached directly or indirectly. For example, the tag may be covalently attached at the N-terminus of the polypeptide sequence, or at the C-terminus of the polypeptide sequence. This can be achieved by recombinant expression of a fusion protein comprising the polypeptide and the tag, or by standard conjugation techniques that links the polypeptide to the tag. The tag may be attached to the side chain functional group of an amino acid residue of the polypeptide using standard conjugation techniques. Alternatively, the tag may be attached non-covalently.

Attachment of the tag may be direct, or indirect (through a linker). Suitable linkers are known to those skilled in the art and include, e.g., straight or branched-chain carbon linkers, heterocyclic carbon linkers, carbohydrate linkers and polypeptide linkers.

In a certain embodiment, cleavable linkers may be used to attach the molecule of interest to the tag. This allows for the tag to be separated from the purified complex, for example by the addition of an agent capable of cleaving the linker. A number of different cleavable linkers are known to those of skill in the art. Such linkers may be cleaved for example, by irradiation of a photolabile bond or acid-catalyzed hydrolysis. There are also polypeptide linkers which incorporate a protease recognition site and which can be cleaved by the addition of a suitable protease enzyme.

When a complex comprising the gL protein (or fragment thereof) is purified, the tag can be attached to other constituent(s) of the complex. For example, when purifying CMV pentameric complex, a tag may be attached to pUL128, pUL130, or pUL131.

5. Pharmaceutical Compositions and Administration

The invention also provides pharmaceutical compositions comprising the CMV proteins, complexes, and nucleic acids described herein. The invention also provides pharmaceutical compositions comprising nucleic acid encoding CMV proteins, complexes, and nucleic acids described herein.

The CMV proteins, complexes, and nucleic acids described herein can be incorporated into an immunogenic composition, or a vaccine composition. Such compositions can be used to raise antibodies in a mammal (e.g. a human).

The invention provides pharmaceutical compositions comprising the CMV proteins, complexes, and nucleic acids described herein, and processes for making a pharmaceutical composition involving combining the CMV proteins, complexes, and nucleic acids described herein with a pharmaceutically acceptable carrier. The pharmaceutical compositions of the invention typically include a pharmaceutically acceptable carrier, and a thorough discussion of such carriers is available in Remington: The Science and Practice of Pharmacy.

The pH of the composition is usually between about 4.5 to about 11, such as between about 5 to about 11, between about 5.5 to about 11, between about 6 to about 11, between about 5 to about 10.5, between about 5.5 to about 10.5, between about 6 to about 10.5, between about 5 to about 10, between about 5.5 to about 10, between about 6 to about 10, between about 5 to about 9.5, between about 5.5 to about 9.5, between about 6 to about 9.5, between about 5 to about 9, between about 5.5 to about 9, between about 6 to about 9, between about 5 to about 8.5, between about 5.5 to about 8.5, between about 6 to about 8.5, between about 5 to about 8, between about 5.5 to about 8, between about 6 to about 8, about 4.5, about 5, about 6.5, about 6, about 6.5, about 7, about 7.5, about 8, about 8.5, about 9, about 9.5, about 10, about 10.5, about 11, etc. Stable pH may be maintained by the use of a buffer e.g. a Tris buffer, a citrate buffer, a phosphate buffer, or a histidine buffer. Thus a composition will generally include a buffer.

A composition may be sterile and/or pyrogen free. Compositions may be isotonic with respect to humans.

A composition comprises an immunologically effective amount of its antigen(s). An "immunologically effective amount" is an amount which, when administered to a subject, is effective for eliciting an antibody response against the antigen. This amount can vary depending upon the health and physical condition of the individual to be treated, their age, the capacity of the individual's immune system to synthesize antibodies, the degree of protection desired, the formulation of the vaccine, the treating doctors assessment of the medical situation, and other relevant factors. It is expected that the amount will fall in a relatively broad range that can be determined through routine trials. The antigen content of compositions of the invention will generally be expressed in terms of the mass of protein per dose. A dose of 10-500 µg (e.g. 50 µg) per antigen can be useful.

Immunogenic compositions may include an immunological adjuvant. Exemplary adjuvants include mineral-containing compositions; oil emulsions; saponin formulations; virosomes and virus-like particles; bacterial or microbial derivatives; bioadhesives and mucoadhesives; liposomes; polyoxyethylene ether and polyoxyethylene ester formulations; polyphosphazene (pcpp); muramyl peptides; imidazoquinolone compounds; thiosemicarbazone compounds; tryptanthrin compounds; human immunomodulators; lipopeptides; benzonaphthyridines; microparticles; immunostimulatory polynucleotide (such as RNA or DNA; e.g., CpG-containing oligonucleotides).

For example, the composition may include an aluminum salt adjuvant, an oil in water emulsion (e.g. an oil-in-water emulsion comprising squalene, such as MF59 or AS03), a TLR7 agonist (such as imidazoquinoline or imiquimod), or a combination thereof. Suitable aluminum salts include hydroxides (e.g. oxyhydroxides), phosphates (e.g. hydroxyphosphates, orthophosphates), (e.g. see chapters 8 & 9 of Vaccine Design (1995) eds. Powell & Newman. ISBN: 030644867X. Plenum), or mixtures thereof. The salts can take any suitable form (e.g. gel, crystalline, amorphous, etc.), with adsorption of antigen to the salt being an example. The concentration of $Al^{+3}$ in a composition for administration to a patient may be less than 5 mg/ml e.g. <4 mg/ml, <3 mg/ml, <2 mg/ml, <1 mg/ml, etc. A preferred range is between 0.3 and 1 mg/ml. A maximum of 0.85 mg/dose is preferred. Aluminum hydroxide and aluminum phosphate adjuvants are suitable for use with the invention.

One suitable immunological adjuvant comprises a compound of Formula (I) as defined in WO2011/027222, or a pharmaceutically acceptable salt thereof, adsorbed to an aluminum salt. Many further adjuvants can be used, including any of those disclosed in Powell & Newman (1995).

Compositions may include an antimicrobial, particularly when packaged in multiple dose format. Antimicrobials such as thimerosal and 2 phenoxyethanol are commonly found in vaccines, but sometimes it may be desirable to use either a mercury-free preservative or no preservative at all.

Compositions may comprise detergent e.g. a polysorbate, such as polysorbate 80. Detergents are generally present at low levels e.g. <0.01%.

Compositions may include sodium salts (e.g. sodium chloride) to give tonicity. A concentration of 10±2 mg/ml NaCl is typical, e.g., about 9 mg/ml.

In another aspect, the invention provides a method of inducing an immune response against cytomegalovirus (CMV), comprising administering to a subject in need thereof an immunologically effective amount of the immunogenic composition describe herein, which comprises the proteins, DNA molecules, RNA molecules (e.g., self-replicating RNA molecules), or VRPs as described above.

In certain embodiments, the immune response comprises the production of neutralizing antibodies against CMV. In certain embodiments, the neutralizing antibodies are complement-independent.

The immune response can comprise a humoral immune response, a cell-mediated immune response, or both. In some embodiments an immune response is induced against each delivered CMV protein. A cell-mediated immune response can comprise a Helper T-cell (Th) response, a CD8+ cytotoxic T-cell (CTL) response, or both. In some embodiments the immune response comprises a humoral immune response, and the antibodies are neutralizing antibodies. Neutralizing antibodies block viral infection of cells. CMV infects epithelial cells and also fibroblast cells. In some embodiments the immune response reduces or prevents infection of both cell types. Neutralizing antibody responses can be complement-dependent or complement-independent. In some embodiments the neutralizing antibody response is complement-independent. In some embodiments the neutralizing antibody response is cross-neutralizing; i.e., an antibody generated against an administered composition neutralizes a CMV virus of a strain other than the strain used in the composition.

A useful measure of antibody potency in the art is "50% neutralization titer." To determine 50% neutralization titer, serum from immunized animals is diluted to assess how dilute serum can be yet retain the ability to block entry of 50% of viruses into cells. For example, a titer of 700 means that serum retained the ability to neutralize 50% of virus after being diluted 700-fold. Thus, higher titers indicate more potent neutralizing antibody responses. In some embodiments, this titer is in a range having a lower limit of about 200, about 400, about 600, about 800, about 1000, about 1500, about 2000, about 2500, about 3000, about 3500, about 4000, about 4500, about 5000, about 5500, about 6000, about 6500, or about 7000. The 50% neutralization titer range can have an upper limit of about 400, about 600, about 800, about 1000, about 1500, about 2000, about 2500, about 3000, about 3500, about 4000, about 4500, about 5000, about 5500, about 6000, about 6500, about 7000, about 8000, about 9000, about 10000, about 11000, about 12000, about 13000, about 14000, about 15000, about 16000, about 17000, about 18000, about 19000, about 20000, about 21000, about 22000, about 23000, about 24000, about 25000, about 26000, about 27000, about 28000, about 29000, or about 30000. For example, the 50% neutralization titer can be about 3000 to about 25000. "About" means plus or minus 10% of the recited value.

Compositions of the invention will generally be administered directly to a subject. Direct delivery may be accomplished by parenteral injection (e.g. subcutaneously, intraperitoneally, intravenously, intramuscularly, or to the interstitial space of a tissue), or by any other suitable route. For example, intramuscular administration may be used e.g. to the thigh or the upper arm. Injection may be via a needle (e.g. a hypodermic needle), but needle-free injection may alternatively be used. A typical intramuscular dosage volume is about 0.5 ml.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The subject may be an animal, preferably a vertebrate, more preferably a mammal. Exemplary subject includes, e.g., a human, a cow, a pig, a chicken, a cat or a dog, as the pathogens covered herein may be problematic across a wide range of species. Where the vaccine is for prophylactic use, the human is preferably a child (e.g., a toddler or infant), a teenager, or an adult; where the vaccine is for therapeutic use, the human is preferably a teenager or an adult. A vaccine intended for children may also be administered to adults, e.g., to assess safety, dosage, immunogenicity, etc.

Vaccines of the invention may be prophylactic (i.e. to prevent disease) or therapeutic (i.e. to reduce or eliminate the symptoms of a disease). The term prophylactic may be considered as reducing the severity of or preventing the onset of a particular condition. For the avoidance of doubt, the term prophylactic vaccine may also refer to vaccines that ameliorate the effects of a future infection, for example by reducing the severity or duration of such an infection.

Isolated and/or purified CMV proteins, complexes, and nucleic acids described herein can be administered alone or as either prime or boost in mixed-modality regimes, such as a RNA prime followed by a protein boost. Benefits of the RNA prime protein boost strategy, as compared to a protein prime protein boost strategy, include, for example, increased antibody titers, a more balanced IgG1:IgG2a subtype profile, induction of TH1-type CD4+ T cell-mediated immune response that was similar to that of viral particles, and reduced production of non-neutralizing antibodies. The RNA prime can increase the immunogenicity of compositions regardless of whether they contain or do not contain an adjuvant.

In the RNA prime-protein boost strategy, the RNA and the protein are directed to the same target antigen. Examples of suitable modes of delivering RNAs include virus-like replicon particles (VRPs), alphavirus RNA, replicons encapsulated in lipid nanoparticles (LNPs) or formulated RNAs, such as replicons formulated with cationic nanoemulsions (CNEs). Suitable cationic oil-in-water nanoemulsions are disclosed in WO2012/006380 e.g. comprising an oil core (e.g. comprising squalene) and a cationic lipid (e.g. DOTAP, DMTAP, DSTAP, DC-cholesterol, etc.).

WO2012/051211 discloses that antibodies to the pentameric complex are produced in mice that have been immunized with VRPs and formulated RNAs (CNEs and LNPs) that encode the protein constituents of the pentameric complex. These antibodies have been found to be capable of neutralizing CMV infection in epithelial cells. The RNA prime-protein boost regimen may involve first (e.g. at weeks 0-8) performing one or more priming immunization(s) with RNA (which could be delivered as VRPs, LNPs, CNEs, etc.) that encodes one or more of the protein components of a CMV protein complex of the invention and then perform one or more boosting immunization(s) later (e.g. at weeks 24-58) with: an isolated CMV protein complex of the invention, optionally formulated with an adjuvant or a purified CMV protein complex of the invention, optionally formulated with an adjuvant.

In some embodiments, the RNA molecule is encapsulated in, bound to or adsorbed on a cationic lipid, a liposome, a cochleate, a virosome, an immune-stimulating complex, a microparticle, a microsphere, a nanosphere, a unilamellar vesicle, a multilamellar vesicle, an oil-in-water emulsion, a water-in-oil emulsion, an emulsome, a polycationic peptide, a cationic nanoemulsion, or combinations thereof.

Also provided herein are kits for administration of nucleic acid (e.g., RNA), purified proteins, and purified complexes described herein, and instructions for use. The invention also provides a delivery device pre-filled with a composition or a vaccine disclosed herein.

The pharmaceutical compositions described herein can be administered in combination with one or more additional therapeutic agents. The additional therapeutic agents may include, but are not limited to antibiotics or antibacterial agents, antiemetic agents, antifungal agents, anti-inflammatory agents, antiviral agents, immunomodulatory agents, cytokines, antidepressants, hormones, alkylating agents, antimetabolites, antitumor antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferons, ribavirin, hormones, and other toll-like receptor modulators, immunoglobulins (Igs), and antibodies modulating Ig function (such as anti-IgE (omalizumab)).

In certain embodiments, the compositions disclosed herein may be used as a medicament, e.g., for use in inducing or enhancing an immune response in a subject in need thereof, such as a mammal.

In certain embodiments, the compositions disclosed herein may be used in the manufacture of a medicament for inducing or enhancing an immune response in a subject in need thereof, such as a mammal.

One way of checking the efficacy of therapeutic treatment involves monitoring pathogen infection after administration of the compositions or vaccines disclosed herein. Another way of checking the efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses are determined post-immunization but pre-challenge whereas antigen-specific mucosal antibody responses are determined post-immunization and post-challenge.

This invention is further illustrated by the following examples which should not be construed as limiting.

EXAMPLES

Example 1: Materials and Methods

Sequence and Structure Analysis.

gL sequences of CMV, VZV and HSV1 and HSV2 were aligned using CLUSTALW (Hyper Text Transfer Protocol Secure (https)://npsa-prabi.ibcp.fr/cgi-bin/npsa_automat.pl?page=npsa_clustalw.html) and manually adjusted to align residues contributed to conserved β-strands in VZV and HSV2.

Expression of Penta and gH/gL Complex.

Wild type (WT) pentameric complex ("penta") or penta with gL mutations ("LSG" and "IDG" mutant) were expressed using a two vector system with gH and gL in one vector, and three ULs in the other. The sequence of IRES (internal ribosome entry site) separates different genes in each vector. gH has a C-terminal 6×His tag (SEQ ID NO: 11), and UL130 has a cleavable C-terminal strep-tag. DNA of the two vectors with 1 mg of total DNA for every liter of culture were transfected into Expi293 cells using Expifectamine transfection kit (Life Technologies) following the manufacture's protocol. Cells were grown to ~2.5×$10^6$ cells/mL on the day of transfection with viability>97% in shaker flasks. The transfected cells were grown for three days to ~8×$10^6$ cells/mL with viability~60% in shaker incubator operated at 37° C., 150 rpm and 8% $CO_2$. Supernatants of the expression media were harvested by centrifugation at 4200 rpm for 30 minutes.

WT gH/gL or gH/gL with gL mutations were expressed using the vector containing both gH and gL in the same way as described above.

N-Terminal Sequencing.

N-terminal sequencing was used to identify unknown bands visible by SDS pages and western blots (WBs) of affinity purified WT penta. Penta on a SDS page was transferred to an ethanol activated PVDF membrane, which was stained by 0.02% Coomassie Brilliant blue in 40% methanol, then washed in distilled water several times before air dried completely. Bands of interest were cut out and shipped to Tufts University Protein Core Facility for sequencing.

Purification and Western Blot Analysis.

Harvested supernatant was concentrated and buffer exchanged into affinity column binding buffer (50 mM Hepes pH7.0, 150 mM NaCl, and 1 mM EDTA) using a KrosFlo Research II TFF system and hollow Fiber Cartridge (Spectrumlabs). Concentrated supernatant was loaded to StrepTrap HP cartridge (GE Life Sciences), and eluted with elution buffer (50 mM Hepes pH 7.0, 150 mM NaCl, 2.5 mM desthiobiotin, and 1 mM EDTA). Peak fractions from the eluate were analyzed by SDS-PAGE and western blotting using antibodies against either gL or the His-tag placed at the C-terminus of gH.

Immunization Studies in Mice.

Ten mice per group were immunized with purified WT or mutant pentameric complex gH/gL/pUL128/pUL130/pUL131 adjuvanted with MF59 at the three different doses 0.03 μg, 0.1 μg and 1 μg with three injections at three week intervals. Serum samples were heat-inactivated at 56° C. for 30 min, serially diluted in two-fold steps (two replicates per dilution), mixed with an equal volume of HCMV virus diluted to a target concentration of 200-250 infected cells/counting field in media±10% guinea pig complement (Cedarlane Labs, Burlington, N.C., USA), and incubated for 2 h at 3TC/5% $CO_2$. These serum/virus samples were added to ARPE-19 cells or MRC-5 cells prepared in 96-well half-area cell culture plates (Corning Inc., Corning, N.Y., USA). The infected monolayers were incubated for 48 hours (±8 h) at 37° C./5% CO2, fixed with 10% buffered formalin (EMD Chemicals Inc., Gibbstown, N.J., USA) for one hour and washed three times with wash buffer (PBS/0.05% Tween-20), blocked with PBS/2.5% fetal bovine serum, 0.5% saponin, 0.1% sodium azide for one hour at room temperature. The plates were washed three times, taped dry and incubated in a 25° C. humid incubator for one hour. The plates were then incubated for one hour at room temperature with anti-HCMV IE1 antibody derived from hybridoma L14 (diluted in saponin buffer). Plates were washed three times and incubated for one hour with anti-mouse IgG conjugated with AlexaFluor 488 (diluted in saponin buffer), and then washed three times with PBS/0.05% Tween-20. The fluorescent cells were counted using an Immunospot S5 UV Analyzer (Cellular Technology Limited, Shaker Heights, Ohio, USA), and the 50% neutralization titer, defined as the reciprocal of the serum dilution yielding 50% reduction in the infected cell count (relative to infected cell count in diluent plus virus control wells), was calculated by linear regression interpolation between the two dilutions with wells yielding average infected cell counts above and below the 50% value.

Example 2: Results 1. gL Clipping Occurs Next to a Conserved β-Strand

N-terminal sequencing determined that a band in identified by western blot using an antibody to gL begins with gL residue 97. Thus the gH/gL/pUL128/pUL130/pUL131 pentameric complex expressed in mammalian cells contains a population of gL proteins clipped between gL residues Asn97 and Ser98. Structure based sequence alignment further disclosed that the clipping site is in a loop region next to a β-strand conserved in both VZV and HSV-2 gH/gL structures (FIG. 1).

Various mutations introduced into the gL sequence in the vicinity of this clipping site resulted in a reduction in the amount of gL clipping. Addition mutations inserted between two and five residues with a mix of polar and nonpolar residues into the cleavage site. Deletion mutations deleted from one to three residues around the cleavage site. Substitution mutations changed Ala96 to hydrophobic residues or residues with large side-chains; changed Asn97 to polar residues with either smaller or larger side-chains, or to nonpolar residues; or changed Ser98 to residues with small side-chains having either a polar or nonpolar character.

2. Comparison of Various Mutant gH/gL with Wild Type gH/gL

Figure 2:
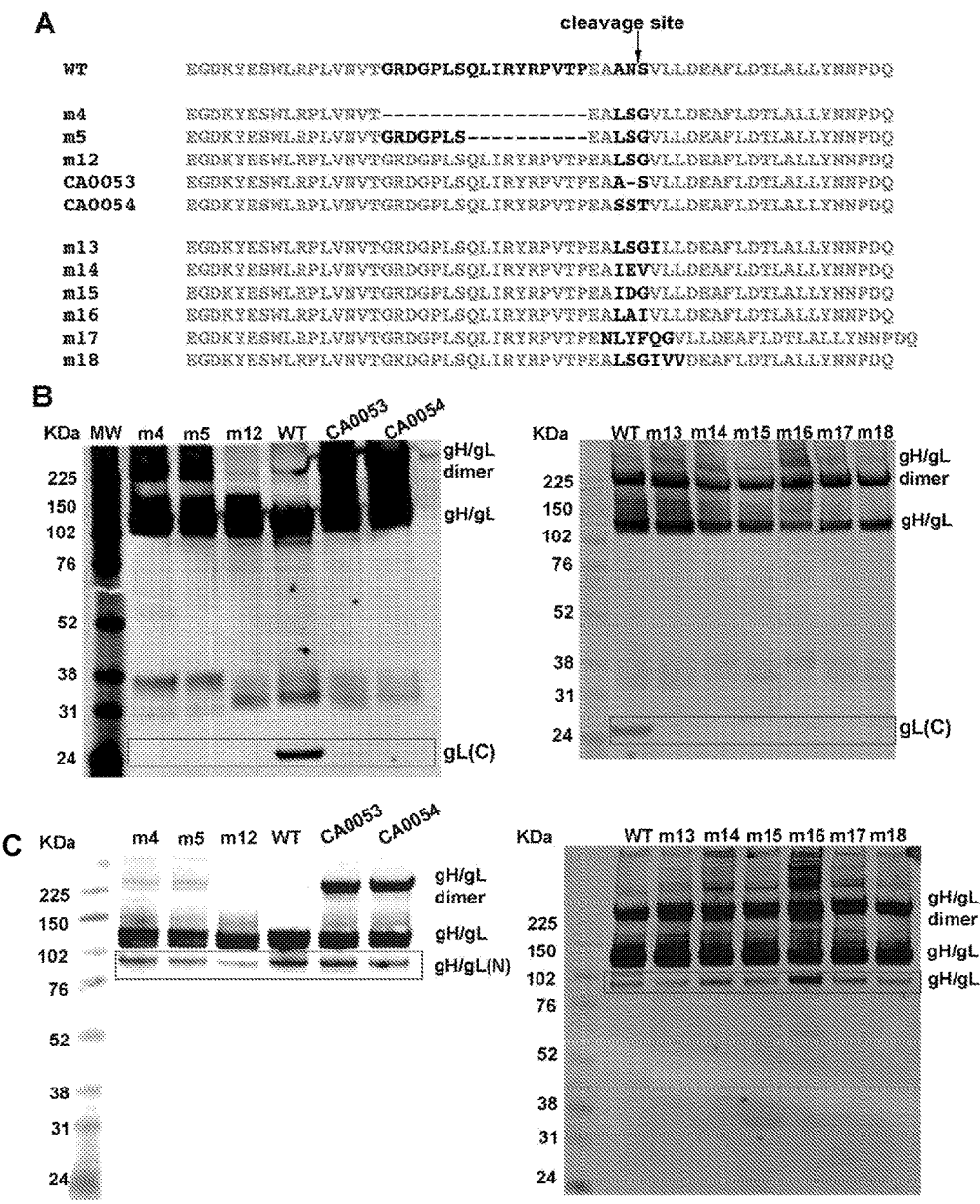
FIG. 2A shows the partial sequences of gL mutants (SEQ ID NOS 15-26, respectively, in order of appearance).
FIG. 2B shows the result of western blot using anti-gL antibodies.
FIG. 2C shows the result of western blot using anti-His antibodies.

FIG. 2A shows various mutant gL proteins that were tested. gH/gL complexes containing various gL mutations were expressed in Expi293 cells and compared to WT gH/gL. Mutations at the Protease Recognition Site reduced gL clipping in the expressed gH/gL complexes. For example, an anti-gL western blot of WT raw supernatant showed a clearly visible band of gL fragment with residue 98 at its N-terminus, as determined by N-terminal sequencing. In contrast, a similar band was not detected in the "LSG" mutant and was either not detected or significantly reduced in the "delta Asn97" and "SST" mutants (FIG. 2).

The three residue variants introduced in the vicinity of the clipping site reduced clipping to a greater extent than a single residue variant in the vicinity of the clipping site. The "LSG" mutant reduced the intensity of gL clipping band most significantly in anti-His western blot. In addition, removing the 17-residue insertion enhanced the intensity of the gL clipping band observed by western blot, gH/gL(N), suggesting that this insertion may protect the cleavage site (FIG. 2C).

3. Comparison of "LSG" and "IDG" Mutant Penta with Wild Type Pentamer

Figure 3:
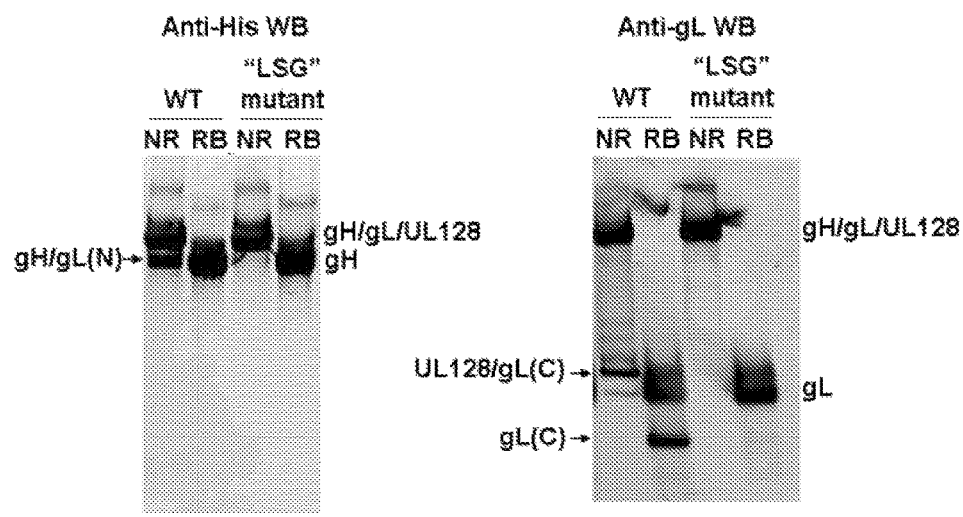
FIG. 3 shows western blot analysis of WT and LSG mutant penta using either non-reduced (NR) or reduced and boiled (RB) protein samples.
Figure 4:
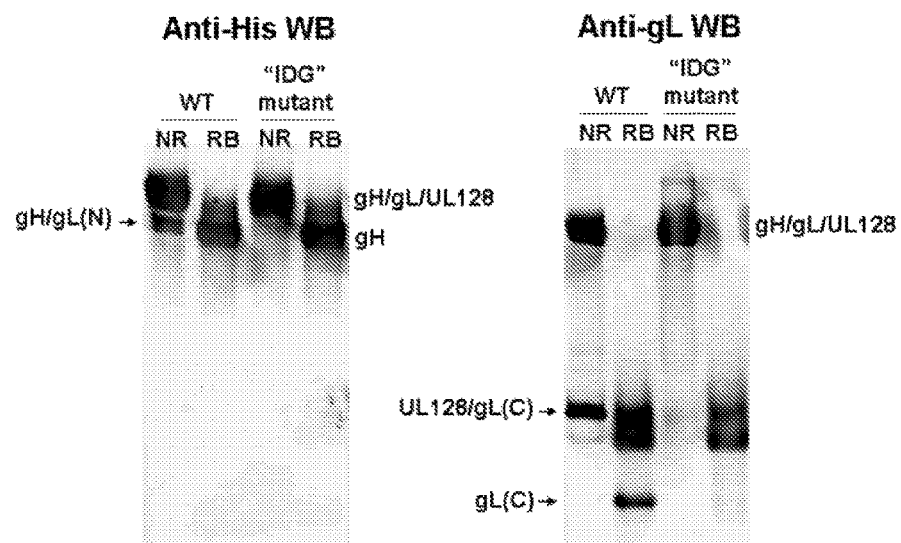
FIG. 4 shows western blot analysis of WT and IDG mutant penta using either non-reduced (NR) or reduced and boiled (RB) protein samples.

To analyze whether the "LSG and "IDG" mutants also eliminated or reduced gL clipping in the gH/gL/pUL128/pUL130/pUL131 pentamer, affinity purified WT and mutant pentamer were analyzed by anti-His and anti-gL western blots. In the anti-His western blot of WT pentamer, there is a pronounced band with smaller molecular weight than the full-length gH/gL, consistent with a complex of gH and the N-terminal region of gL after clipping. Note that this N-terminal fragment of gL is not recognized by the anti-gL antibody. In the anti-gL western blot, the C-terminal region of gL, beginning with residue 98 as determined by N-terminal sequencing, forms a complex with UL128 in a non-reduced sample. The same C-terminal fragment of gL by itself was observed in a reduced sample. In comparison, those bands resulting from gL clipping were not detected in either the "LSG" or "IDG" mutant pentamers (FIGS. 3 and 4). Both "LSG" and "IDG" mutants produced pentamer that behaved similarly to WT pentamer complex. Therefore those mutations do not affect the assembly of the gH/gL/pUL128/pUL130/pUL131 pentamer complex, but eliminated the proteolytic clipping of the gL protein (FIG. 5A).

Figure 5:
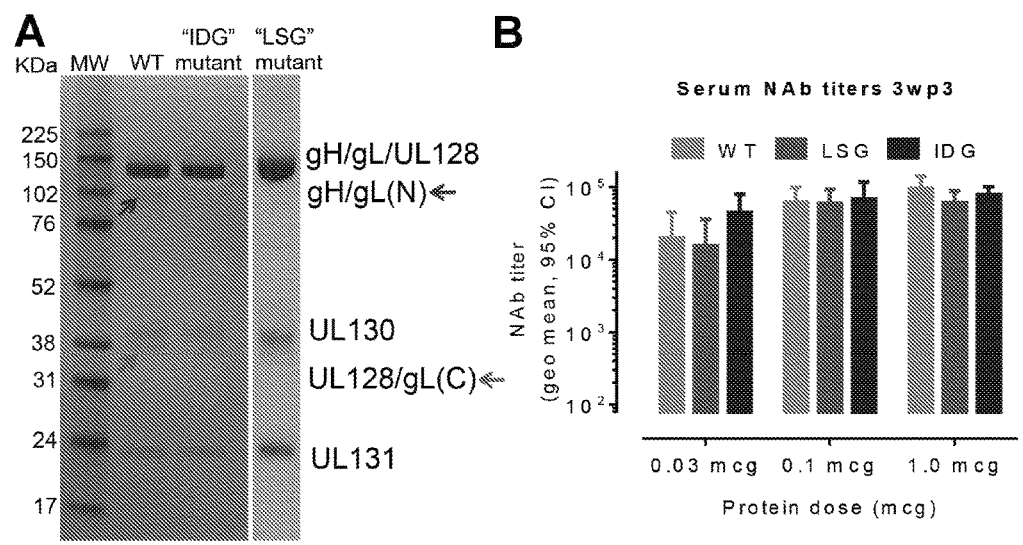
FIG. 5A shows purified WT penta and IDG and LSG mutant penta.
FIG. 5B shows the neutralization antibody titer (NAB) of mouse serum immunized with WT, LSG mutant, or IDG mutant penta adjuvented with MF59.

Immunogenicity analysis showed that the LSG and IDG mutants did not compromise the immunogenicity of the gH/gL/pUL128/pUL130/pUL131 pentameric complex (FIG. 5B).

The fragment of gL that resulted from clipping was detected during the expression of the gH/gL, gH/gL/gO (data not shown) and gH/gL/pUL128/pUL130/pUL131 complexes. The clipping sites in these three complexes are identical, between gL residues 97 and 98. Therefore, mutations that prevent gL clipping during the expression of gH/gL also prevent gL clipping during the expression of the gH/gL/gO and gH/gL/pUL128/pUL130/pUL131 pentamer complexes.

With as few as three residue substitutions or a single deletion, gL clipping can, respectively, be eliminated or significantly reduced. The location of these mutations is not expected to affect the conserved secondary structure in their vicinity. This allows the production of homogenous gH/gL/pUL128/pUL130/pUL131 pentamer with its three dimensional structure, and antigenicity/immunogenicity largely unaffected. We conclude that the strategy of mutating the sequence in the vicinity of the clipping site with homologous sequence proved effective.

The various features and embodiments of the present invention, referred to in individual sections above apply, as appropriate, to other sections, mutatis mutandis. Consequently, features specified in one section may be combined with features specified in other sections, as appropriate.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

The practice of the present invention will employ, unless otherwise indicated, conventional methods of chemistry, biochemistry, molecular biology, immunology and pharmacology, within the skill of the art. Such techniques are explained fully in the literature. The term "comprising" encompasses "including" as well as "consisting" e.g. a composition "comprising" X may consist exclusively of X or may include something additional, e.g. X+Y.

The term "consisting essentially of" means that the composition, method or structure may include additional ingredients, steps and/or parts, but only if the additional ingredients, steps and/or parts do no materially alter the basic and novel characteristics of the claimed composition, method or structure. The term "consisting of" is generally taken to mean that the invention as claimed is limited to those elements specifically recited in the claim (and may include their equivalents, insofar as the doctrine of equivalents is applicable).

Those skilled in the art will recognize, or be able to ascertain using no more than routine experimentation, many equivalents to the specific embodiments of the invention described herein. Such equivalents are intended to be encompassed by the following embodiments.

1. A recombinant cytomegalovirus (CMV) gL protein, or a complex-forming fragment thereof, wherein said gL protein or fragment comprises a mutation within Protease Recognition Site, wherein said mutation reduces protease cleavage at said Protease Recognition Site as compared to a control.
2. The gL protein or fragment of embodiment 1, wherein said mutation comprises addition, deletion, substitution, or a combination thereof, of an amino acid residue.
3. The gL protein or fragment of embodiment 1 or 2, wherein three or more residues of said Protease Recognition Site form a β-strand, and said mutation maintains the β-strand conformation.
4. The gL protein or fragment of any one of embodiments 1-3, wherein said mutation results in no more than 20% (molar percentage) of gL cleaved at said Protease Recognition Site when recombinantly expressed in a mammalian host cell.

5. The gL protein or fragment of any one of embodiments 1-4, wherein said mutation comprises addition of one or more amino acid residues.

6. The gL protein or fragment of any one of embodiments 1-5, wherein said mutation comprises addition of two to five amino acid residues.

7. The gL protein or fragment of embodiment 6, wherein said two to five amino acid residues comprise both polar residue(s) and non-polar residue(s).

8. The gL protein or fragment of any one of embodiments 1-7, wherein said mutation comprises addition of one or more residues between residues N97 and S98.

9. The gL protein or fragment of any one of embodiments 1-8, wherein said mutation comprises addition of F, Q, FQ or QF between residues N97 and S98.

10. The gL protein or fragment of any one of embodiments 1-9, wherein said mutation comprises deletion of one or more amino acid residues.

11. The gL protein or fragment of any one of embodiments 1-10, wherein said mutation comprises deletion of one to three amino acid residues.

12. The gL protein or fragment of any one of embodiments 1-11, wherein said mutation comprises deletion of a residue selected from the group consisting of: V91, T92, P93, E94, A95, A96, N97, S98, V99, L100, L101, D102 and a combination thereof.

13. The gL protein or fragment of any one of embodiments 1-12, wherein said mutation comprises deletion of a residue selected from the group consisting of: A95, A96, N97, and a combination thereof.

14. The gL protein or fragment of any one of embodiments 1-13, wherein said mutation comprises deleting N97.

15. The gL protein or fragment of any one of embodiments 1-14, wherein said mutation comprises substituting a residue with a corresponding residue from a gL protein of another herpes virus.

16. The gL protein or fragment of embodiment 15, wherein said gL protein from another herpes virus is a gL protein from HSV1, HSV2, VZV, EBV, PrV, or bovine herpesvirus 5.

17. The gL protein or fragment of any one of embodiments 1-16, wherein said mutation comprises substituting g A96 with a non-polar residue or with a residue that comprises a large side chain.

18. The gL protein or fragment of any one of embodiments 1-17, wherein said mutation comprises substituting A96 with I, L, V or S.

19. The gL protein or fragment of any one of embodiments 1-18, wherein said mutation comprises substituting A95 with R, L, E or N.

20. The gL protein or fragment of any one of embodiments 1-19, wherein said mutation comprises substituting E94 with A or L.

21. The gL protein or fragment of any one of embodiments 1-20, wherein said mutation comprises substituting N97 with a polar residue or a non-polar residue.

22. The gL protein or fragment of embodiment 21, wherein said polar residue comprises a small side chain.

23. The gL protein or fragment of embodiment 21, wherein said polar residue comprises a large side chain.

24. The gL protein or fragment of any one of embodiments 1-23, wherein said mutation comprises substituting N97 with S, D, E, A, T or Y.

25. The gL protein or fragment of any one of embodiments 1-24, wherein said mutation comprises substituting N97 with S or D.

26. The gL protein or fragment of any one of embodiments 1-25, wherein said mutation comprises substituting S98 with an amino acid residue with a small side chain.

27. The gL protein or fragment of any one of embodiments 1-26, wherein said mutation comprises substituting S98 with G, T, V, or I.

28. The gL protein or fragment of any one of embodiments 1-27, wherein said mutation comprises substituting S98 with G, or T.

29. The gL protein or fragment of any one of embodiments 1-28, wherein said mutation comprises substituting V99 with I.

30. The gL protein or fragment of any one of embodiments 1-29, wherein said mutation comprises substituting L100 with an amino acid residue with F or V.

31. The gL protein or fragment of any one of embodiments 1-30, wherein said mutation comprises substituting L101 with an amino acid residue with V or I.

32. The gL protein or fragment of any one of embodiments 1-31, wherein said gL protein or fragment comprises an Insert Region at the N-terminus of the Protease Recognition Site.

33. The gL protein or fragment of any one of embodiments 1-32, wherein said mutation comprises introducing a non-naturally occurring amino acid residue.

34. The gL protein or fragment of any one of embodiments 1-33, wherein said mutation comprises introducing an amino acid residue comprising a bulky side chain.

35. A CMV complex comprising the recombinant gL protein or fragment of any one of embodiments 1-34.

36. The complex of embodiment 35, comprising a CMV protein selected from the group consisting of gH, gL, pUL128, pUL130, pUL131, gO, a complex-forming fragment thereof, and a combination thereof.

37. The complex of embodiment 35 or 36, wherein said complex is a pentameric complex comprising: gH or a pentamer-forming fragment thereof, gL or a pentamer-forming fragment thereof, pUL128 or a pentamer-forming fragment thereof, pUL130 or a pentamer-forming fragment thereof, and pUL131 or a pentamer-forming fragment thereof.

38. The complex of embodiment 35 or 36, wherein said complex is a gH/gL complex comprising: gH or a complex-forming fragment thereof, and gL or a complex-forming fragment thereof.

39. The complex of embodiment 35 or 36, wherein said complex is a trimeric complex comprising: gH or a complex-forming fragment thereof, gL or a complex-forming fragment thereof, and gO or a complex-forming fragment thereof 40. An immunogenic composition comprising the recombinant CMV gL protein or fragment of any of one of embodiments 1-34, or the complex of any one of embodiment 35-39.

41. The immunogenic composition of embodiment 40, further comprising an adjuvant.

42. The immunogenic composition of embodiment 41, wherein said adjuvant comprises an aluminum salt, a TLR7 agonist, an oil-in-water emulsion, or a combination thereof.

43. The immunogenic composition of embodiment 42, wherein said oil-in-water emulsion is MF59.

44. An isolated nucleic acid comprising a polynucleotide sequence encoding the recombinant CMV gL protein or fragment of any one of embodiments 1-34.

45. The isolated nucleic acid of embodiment 44, wherein said isolated nucleic acid is an RNA, preferably a self-replicating RNA.

46. The isolated nucleic acid of embodiment 45, wherein said self-replicating RNA is an alphavirus replicon.

47. An alphavirus replication particle (VRP) comprising the alphavirus replicon of embodiment 46.

48. An immunogenic composition comprising the nucleic acid of any one of embodiments 44-46.

49. An immunogenic composition comprising the VRP of embodiment 47.

50. The immunogenic composition of embodiment 48 or 49, further comprising an adjuvant.

51. The immunogenic composition of embodiment 50, wherein said adjuvant comprises an aluminum salt, a TLR7 agonist, an oil-in-water emulsion (such as MF59), or a combination thereof.

52. A host cell comprising the nucleic acid of any one of embodiments 44-46.

53. The host cell of embodiment 52, wherein said nucleic acid is a DNA.

54. The host cell of embodiment 53, wherein said host cell is a mammalian cell.

55. The host cell of embodiment 54, wherein said mammalian cell is a CHO cell or HEK-293 cell.

56. The host cell of any one of embodiments 53-55, wherein said DNA encoding the CMV gL protein or fragment thereof is integrated into the genomic DNA of said host cell.

57. The host cell of any one of embodiments 52-56, wherein said host cell comprises one or more polynucleotide sequences encoding CMV pentameric complex, said pentameric complex comprising: gH or a pentamer-forming fragment thereof, gL or a pentamer-forming fragment thereof, pUL128 or a pentamer-forming fragment thereof, pUL130 or a pentamer-forming fragment thereof, and pUL131 or a pentamer-forming fragment thereof.

58. The host cell of embodiment 57, wherein said one or more polynucleotide sequences encoding CMV pentameric complex are integrated into the genomic DNA of said host cell.

59. The host cell of embodiment 57 or 58, wherein said cell, when cultured under a suitable condition, expresses said CMV pentameric complex.

60. The host cell of embodiment 59, wherein said pentameric complex is secreted.

61. A cell culture comprising the host cell of any one of embodiments 52-60, wherein said culture is at least 20 liter in size.

62. A cell culture comprising the host cell of any one of embodiments 52-60, wherein said culture is at least 100 liter in size.

63. A cell culture comprising the host cell of any one of embodiments 57-60, wherein the yield of said pentameric complex is at least 0.05 g/L.

64. A cell culture comprising the host cell of embodiment 63, wherein the yield said pentameric complex is at least 0.1 g/L.

65. A process of producing a recombinant cytomegalovirus (CMV) gL protein, or a complex-forming fragment thereof, comprising:

(i) culturing the host cell of any one of embodiments 52-60 under a suitable condition, thereby expressing said gL protein, or complex-forming fragment thereof; and (ii) harvesting said gL protein, or complex-forming fragment thereof, from the culture.

66. A method of inducing an immune response against cytomegalovirus (CMV), comprising administering to a subject in need thereof an immunologically effective amount of the immunogenic composition of any one of embodiments 40-43 and 48-51.

67. The method of embodiment 66, wherein the immune response comprises the production of neutralizing antibodies against CMV.

68. The method of embodiment 67, wherein the neutralizing antibodies are complement-independent.

69. A method of inhibiting cytomegalovirus (CMV) entry into a cell, comprising contacting the cell with the immunogenic composition of any one of embodiments 40-43 and 48-51.

70. The immunogenic composition of any one of embodiments 40-43 and 48-51 for use in inducing an immune response against cytomegalovirus (CMV).

71. Use of the immunogenic composition of any one of embodiments 40-43 and 48-51 for inducing an immune response against cytomegalovirus (CMV).

72. Use of the immunogenic composition of any one of embodiments 40-43 and 48-51 in the manufacture of a medicament for inducing an immune response against cytomegalovirus (CMV).

SEQUENCES

SEQ ID NO: 1 (gL from HCMV strain Merlin = GI:39842115)
MCRRPDCGFSFSPGPVILLWCCLLLPIVSSAAVSVAPTAAEKVPAECPEL
TRRCLLGEVFEGDKYESWLRPLVNVTGRDGPLSQLIRYRPVTPEAANSVL
LDEAFLDTLALLYNNPDQLRALLTLLSSDTAPRWMTVMRGYSECGDGSPA
VYTCVDDLCRGYDLTRLSYGRSIFTEHVLGFELVPPSLFNVVVAIRNEAT
RTNRAVRLPVSTAAAPEGITLFYGLYNAVKEFCLRHQLDPPLLRHLDKYY
AGLPPELKQTRVNLPAHSRYGPQAVDAR SEQ ID NO: 2 (gL from HCMV strain Towne = GI:239909463)
MCRRPDCGFSFSPGPVALLWCCLLLPIVSSATVSVAPTVAEKVPAECPEL
TRRCLLGEVFQGDKYESWLRPLVNVTRRDGPLSQLIRYRPVTPEAANSVL
LDDAFLDTLALLYNNPDQLRALLTLLSSDTAPRWMTVMRGYSECGDGSPA
VYTCVDDLCRGYDLTRLSYGRSIFTEHVLGFELVPPSLFNVVVAIRNEAT
RTNRAVRLPVSTAAAPEGITLFYGLYNAVKEFCLRHQLDPPLLRHLDKYY
AGLPPELKQTRVNLPAHSRYGPQAVDAR SEQ ID NO: 3 (gL from HCMV strain AD169 = GI:2506510)
MCRRPDCGFSFSPGPVVLLWCCLLLPIVSSVAVSVAPTAAEKVPAECPEL
TRRCLLGEVFQGDKYESWLRPLVNVTRRDGPLSQLIRYRPVTPEAANSVL
LDDAFLDTLALLYNNPDQLRALLTLLSSDTAPRWMTVMRGYSECGDGSPA
VYTCVDDLCRGYDLTRLSYGRSIFTEHVLGFELVPPSLFNVVVAIRNEAT
RTNRAVRLPVSTAAAPEGITLFYGLYNAVKEFCLRHQLDPPLLRHLDKYY
AGLPPELKQTRVNLPAHSRYGPQAVDAR SEQ ID NO: 4 (gL mature protein consisting of amino acid residues 31-278 of SEQ ID NO: 1)
AAVSVAPTAAEKVPAECPELTRRCLLGEVFEGDKYESWLRPLVNVTGRDG
PLSQLIRYRPVTPEAANSVLLDEAFLDTLALLYNNPDQLRALLTLLSSDT
APRWMTVMRGYSECGDGSPAVYTCVDDLCRGYDLTRLSYGRSIFTEHVLG
FELVPPSLFNVVVAIRNEATRTNRAVRLPVSTAAAPEGITLFYGLYNAVK
EFCLRHQLDPPLLRHLDKYYAGLPPELKQTRVNLPAHSRYGPQAVDAR SEQ ID NO: 5 (17 residue insert from gL from HCMV strain Merlin)
GRDGPLSQLIRYRPVTP SEQ ID NO: 6 (gH from HCMV strain Towne = GI:138314)
MRPGLPSYLIVLAVCLLSHLLSSRYGAEAISEPLDKAFHLLLNTYGRPIR
FLRENTTQCTYNSSLRNSTVVRENAISENFFQSYNQYYVEHMPRCLFAGP
LAEQFLNQVDLTETLERYQQRLNTYALVSKDLASYRSFSQQLKAQDSLGE
QPTTVPPPIDLSIPHVWMPPQTTPHGWTESHTTSGLHRPHFNQTCILFDG
HDLLFSTVTPCLHQGFYLIDELRYVKITLTEDFFVVTVSIDDDTPMLLIF
GHLPRVLFKAPYQRDNFILRQTEKHELLVLVKKDQLNRHSYLKDPDFLDA
ALDFNYLDLSALLRNSFHRYAVDVLKSGRCQMLDRRTVEMAFAYALALFA
AARQEEAGAQVSVPRALDRQAALLQIQEFMITCLSQTPPRTTLLLYPTAV
DLAKRALWTPNQITDITSLVRLVYILSKQNQQHLIPQWALRQIADFALKL
HKTHLASFLSAFARQELYLMGSLVHSMLVHTTERREIFIVETGLCSLAEL
SHFTQLLAHPHHEYLSDLYTPCSSSGRRDHSLERLTRLFPDATVPTTVPA
ALSILSTMQPSTLETFPDLFCLPLGESFSALTVSEHVSYVVTNQYLIKGI
SYPVSTTVVGQSLIITQTDSQTKCELTRNMHTTHSITAALNISLENCAFC
QSALLEYDDTQGVINIMYMHDSDDVLFALDPYNEVVVSSPRTHYLMLLKN
GTVLEVTDVVVDATDSRLLMMSVYALSAIIGIYLLYRMLKTC SEQ ID NO: 7 (6 residue insert from gL from HCMV strain Merlin)
NSVLLD SEQ ID NO: 8 (FLAG Tag)
DYKDDDDK SEQ ID NO: 9 (Strep Tag)
AWRHPQFGG SEQ ID NO: 10 (Strep Tag II)
WSHPQFEK SEQ ID NO: 11 (His Tag)
HHHHHH

---

The invention claimed is:

1. A recombinant Human Cytomegalovirus (HCMV) gL protein, or a complex-forming fragment thereof, wherein said gL protein or fragment comprises a mutation at Protease Recognition Site residues 91-102 numbered according to SEQ ID NO: 1, wherein said mutation reduces protease cleavage at said Protease Recognition Site as compared to a control.

2. The gL protein or fragment of claim 1, wherein said mutation comprises addition of one to five amino acid residues.

3. The gL protein or fragment of claim 2, comprising an addition of two to five amino acid residues and wherein said two to five amino acid residues comprise both polar residue(s) and non-polar residue(s).

4. The gL protein or fragment of claim 2, wherein said mutation comprises addition of one to five residues between residues corresponding to N97 and S98 of SEQ ID NO: 1.

5. The gL protein or fragment of claim 4, wherein said mutation comprises addition of F, Q, FQ or QF between residues corresponding to N97 and S98 of SEQ ID NO: 1.

6. The gL protein or fragment of claim 1, wherein said mutation comprises deletion of one to three amino acid residues.

7. The gL protein or fragment of claim 1, wherein said mutation comprises deletion of a residue corresponding to the residue of SEQ ID NO: 1 selected from the group consisting of: V91, T92, P93, E94, A95, A96, N97, S98, V99, L100, L101, D102 and a combination thereof.

8. The gL protein or fragment of claim 1, wherein said mutation comprises substituting a residue with a corresponding residue from the gL protein of another herpes virus.

9. The gL protein or fragment of claim 8, wherein said gL protein from another herpes virus is gL protein from HSV1, HSV2, VZV, EBV, PrV, or bovine herpesvirus 5.

10. The gL protein or fragment of claim 1, wherein said mutation comprises substituting a residue corresponding to the residue of SEQ ID NO: 1 selected from the group consisting of: A96, N97, S98, and a combination thereof.

11. The gL protein or fragment of claim 10, wherein said mutation comprises substituting the residue corresponding to the A96 residue of SEQ ID NO: 1 with another non-polar residue and substituting the residues corresponding to the N97 and S98 residues of SEQ ID NO: 1 with another residue that comprises a small side chain.

12. The gL protein or fragment of claim 11, wherein said residue corresponding to the A96 residue of SEQ ID NO: 1 is substituted to L or I, said residue corresponding to the N97 residue of SEQ ID NO: 1 is substituted to S or D, and said residue corresponding to the S98 residue of SEQ ID NO: 1 is substituted to G.

13. The gL protein or fragment of claim 1, wherein said mutation comprises substituting the residue corresponding to A96 of SEQ ID NO: 1 with a non-polar residue or with a residue that comprises a large side chain.

14. The gL protein or fragment of claim 1, wherein said mutation comprises substituting the residue corresponding to A96 of SEQ ID NO: 1 with I, L, V or S.

15. The gL protein or fragment of claim 1, wherein said mutation comprises substituting the residue corresponding to A95 of SEQ ID NO: 1 with R, L, E or N.

16. The gL protein or fragment of claim 1, wherein said mutation comprises substituting the residue corresponding to E94 of SEQ ID NO: 1 with A or L.

17. The gL protein or fragment of claim 1, wherein said mutation comprises substituting the residue corresponding to N97 of SEQ ID NO: 1 with a polar residue or a non-polar residue.

18. The gL protein or fragment of claim 17, wherein said polar residue comprises a small side chain.

19. The gL protein or fragment of claim 17, wherein said polar residue comprises a large side chain.

20. The gL protein or fragment of claim 1, wherein said mutation comprises substituting the residue corresponding to N97 of SEQ ID NO: 1 with S, D, E, A, T or Y.

21. The gL protein or fragment of claim 1, wherein said mutation comprises substituting the residue corresponding to S98 of SEQ ID NO: 1 with an amino acid residue with a small side chain.

22. The gL protein or fragment of claim 1, wherein said mutation comprises substituting the residue corresponding to S98 of SEQ ID NO: 1 with G, T, V, or I.

23. The gL protein or fragment of claim 1, wherein said mutation comprises substituting the residue corresponding to V99 of SEQ ID NO: 1 with I.

24. The gL protein or fragment of claim 1, wherein said mutation comprises substituting the residue corresponding to L100 of SEQ ID NO: 1 with F or V.

25. The gL protein or fragment of claim 1, wherein said mutation comprises substituting the residue corresponding to L101 of SEQ ID NO: 1 with V or I.

26. The gL protein or fragment of claim 1, wherein said gL protein or fragment comprises an Insert Region at the N-terminus of the Protease Recognition Site.

27. The gL protein or fragment of claim 1, wherein said mutation comprises introducing a non-naturally occurring amino acid residue.

28. The gL protein or fragment of claim 1, wherein said mutation comprises introducing an amino acid residue comprising a bulky side chain.

29. An HCMV complex comprising the recombinant gL protein or fragment of claim 1.

30. The complex of claim 29, wherein said complex is a pentameric complex comprising: gH or a pentamer-forming fragment thereof, gL or a pentamer-forming fragment thereof, pUL128 or a pentamer-forming fragment thereof, pUL130 or a pentamer-forming fragment thereof, and pUL131 or a pentamer-forming fragment thereof.

31. The complex of claim 30, wherein said complex comprises a gH pentamer-forming fragment that lacks a transmembrane domain.

32. An HCMV complex comprising the recombinant gL protein or fragment of claim 10.

33. The complex of claim 32, wherein said complex is a pentameric complex comprising: gH or a pentamer-forming fragment thereof, gL or a pentamer-forming fragment thereof, pUL128 or a pentamer-forming fragment thereof, pUL130 or a pentamer-forming fragment thereof, and pUL131 or a pentamer-forming fragment thereof.

34. The complex of claim 33, wherein said complex comprises a gH pentamer-forming fragment that lacks a transmembrane domain.

35. An isolated nucleic acid comprising a polynucleotide sequence encoding the recombinant gL protein or fragment of claim 1.

36. An isolated nucleic acid comprising a polynucleotide sequence encoding the recombinant gL protein or fragment of claim 10.

37. An isolated nucleic acid comprising a polynucleotide sequence encoding the complex of claim 29.

38. An isolated nucleic acid comprising a polynucleotide sequence encoding the complex of claim 32.

39. A vector comprising the isolated nucleic acid of claim 35.

40. A vector comprising the isolated nucleic acid of claim 36.

41. A vector comprising the isolated nucleic acid of claim 37.

42. A vector comprising the isolated nucleic acid of claim 38.

43. An isolated host cell comprising the isolated nucleic acid of claim 35.

44. An isolated host cell comprising the isolated nucleic acid of claim 36.

45. An isolated host cell comprising the isolated nucleic acid of claim 37.

46. An isolated host cell comprising the isolated nucleic acid of claim 38.

47. A cell culture comprising the host cell of claim 43.
48. A cell culture comprising the host cell of claim 44.
49. A cell culture comprising the host cell of claim 45.
50. A cell culture comprising the host cell of claim 46.

51. An immunogenic composition comprising the recombinant gL protein or fragment of claim 1 and optionally comprising an adjuvant.

52. An immunogenic composition comprising the recombinant gL protein or fragment of claim 10 and optionally comprising an adjuvant.

53. An immunogenic composition comprising the complex of claim 29 and optionally comprising an adjuvant.

54. An immunogenic composition comprising the complex of claim 32 and optionally comprising an adjuvant.

55. A process of producing a recombinant Human Cytomegalovirus (HCMV) gL protein, or a complex-forming fragment thereof, comprising:
   (i) culturing the isolated host cell of claim 43 under a suitable condition, thereby expressing said gL protein, or complex-forming fragment thereof; and
   (ii) harvesting said gL protein, or complex-forming fragment thereof, from the culture.

56. A method of inducing an immune response against Human Cytomegalovirus (HCMV), comprising administering to a subject in need thereof an immunologically effective amount of the immunogenic composition of claim 53.

57. The method of claim 56, wherein the immune response comprises the production of neutralizing antibodies against CMV.

58. The method of claim 57, wherein the neutralizing antibodies are complement-independent.

59. A method of inhibiting Human Cytomegalovirus (HCMV) entry into a cell, comprising contacting the cell with an HCMV complex comprising the recombinant gL protein or fragment of claim 1.

60. A recombinant Human Cytomegalovirus (HCMV) gL protein, or a complex-forming fragment thereof, wherein said gL protein or fragment comprises a mutation at Protease Recognition Site residues 91-102 numbered according to SEQ ID NO: 1.

* * * * *